United States Patent
Mathews et al.

(10) Patent No.: US 8,690,836 B2
(45) Date of Patent: Apr. 8, 2014

(54) AUTO-INJECTOR APPARATUS

(75) Inventors: Colin J. Mathews, Godmanchester (GB); Chris J. Hurlstone, Newport (GB); Ben G. Turner, Leighton Buzzard (GB); Oliver T. Harvey, Cambridge (GB); Dominic C. Reber, Cambridge (GB); John G. Wilmot, Mount Airy, MD (US); Clarence M. Mesa, Boyds, MD (US); Robert L. Hill, Abingdon, MD (US); James R. Stewart, Jr., Leesburg, VA (US)

(73) Assignee: Meridian Medical Technologies, Inc., Columbia, MD (US)

( * ) Notice: Subject to any disclaimer, the term of this patent is extended or adjusted under 35 U.S.C. 154(b) by 586 days.

(21) Appl. No.: 12/624,604

(22) Filed: Nov. 24, 2009

(65) Prior Publication Data
US 2010/0137832 A1 Jun. 3, 2010

(30) Foreign Application Priority Data
Nov. 25, 2008 (GB) .................................. 0821492.6

(51) Int. Cl.
*A61M 5/178* (2006.01)
(52) U.S. Cl.
USPC .......................................... 604/185; 604/136
(58) Field of Classification Search
USPC .................. 604/136, 137, 139, 185, 192, 263
See application file for complete search history.

(56) References Cited

U.S. PATENT DOCUMENTS

| | | | |
|---|---|---|---|
| 1,687,502 A | 10/1928 | Marcy | |
| 2,103,389 A | 12/1937 | Salfisberg | |
| 2,648,463 A | 8/1953 | Scherer | |
| 2,798,488 A * | 7/1957 | Hall | 604/82 |
| 3,081,002 A | 3/1963 | Tauschinski et al. | |
| 3,221,939 A | 12/1965 | Brown | |
| 3,244,173 A | 4/1966 | Berg | |
| 3,332,549 A | 7/1967 | Powell | |
| 3,342,326 A | 9/1967 | Zackheim | |
| 3,647,117 A | 3/1972 | Hargest | |
| 3,670,926 A | 6/1972 | Hill | |
| 3,736,933 A | 6/1973 | Szabo | |
| 4,013,073 A | 3/1977 | Cunningham | |
| 4,019,655 A | 4/1977 | Moeller | |

(Continued)

FOREIGN PATENT DOCUMENTS

WO 03099358 A2 12/2003

OTHER PUBLICATIONS

Exhibit A: Co-pending U.S. Appl. No. 12/624,591, filed Nov. 24, 2009. (not prior art but being cited in the interest of full disclosure).

(Continued)

*Primary Examiner* — Emily Schmidt
(74) *Attorney, Agent, or Firm* — Stephanie J. Monaco

(57) ABSTRACT

An auto-injector apparatus includes a flexible container containing a liquid medicant, a needle communicated with a container, a housing with a container being received in the housing, a pump disposed in the housing and positioned to engage the flexible container and expel the medicant from the container through the needle upon relative movement between the pump and the container, and a main drive spring operably associated with the needle to extend the needle from a first needle position wherein the needle is completely received in the housing to a second needle position wherein the needle protrudes from the housing. The pump may be a roller.

17 Claims, 24 Drawing Sheets

(56) References Cited

U.S. PATENT DOCUMENTS

| | | | |
|---|---|---|---|
| 4,020,836 A | 5/1977 | Cunningham | |
| 4,044,764 A | 8/1977 | Szabo et al. | |
| 4,139,009 A | 2/1979 | Alvarez | |
| 4,163,509 A | 8/1979 | Amneus | |
| 4,196,825 A | 4/1980 | Kincaid | |
| 4,430,079 A | 2/1984 | Thill et al. | |
| 4,548,601 A | 10/1985 | Lary | |
| 4,741,736 A | 5/1988 | Brown | |
| 4,765,512 A | 8/1988 | Bull, Jr. | |
| 4,850,971 A | 7/1989 | Colvin | |
| 4,867,172 A | 9/1989 | Haber et al. | |
| 5,478,316 A | 12/1995 | Bitdinger et al. | |
| 5,527,287 A | 6/1996 | Miskinyar | |
| 5,560,518 A | 10/1996 | Catterall et al. | |
| 5,692,645 A | 12/1997 | Ryu | |
| 5,810,783 A | 9/1998 | Claro | |
| 5,891,096 A | 4/1999 | Hyun et al. | |
| 5,984,912 A | 11/1999 | Niedospial, Jr. et al. | |
| 6,056,718 A | 5/2000 | Funderburk et al. | |
| 6,669,668 B1 | 12/2003 | Kleeman et al. | |
| 6,695,169 B1 | 2/2004 | Dambricourt | |
| 6,726,655 B1 | 4/2004 | Lieberman et al. | |
| 6,808,514 B2 | 10/2004 | Schneider et al. | |
| 6,846,305 B2 | 1/2005 | Smith et al. | |
| 6,979,316 B1 | 12/2005 | Rubin et al. | |
| 7,361,160 B2 | 4/2008 | Hommann et al. | |
| 7,416,540 B2 | 8/2008 | Edwards et al. | |
| 7,431,178 B2 | 10/2008 | Allen | |
| 7,544,188 B2 | 6/2009 | Edwards et al. | |
| 7,648,482 B2 | 1/2010 | Edwards et al. | |
| 7,648,494 B2 | 1/2010 | Kornerup et al. | |
| 2002/0170923 A1 | 11/2002 | Vatman | |
| 2002/0183701 A1 | 12/2002 | Hochman et al. | |
| 2003/0034264 A1* | 2/2003 | Hamai et al. | 206/364 |
| 2003/0050609 A1 | 3/2003 | Sams | |
| 2004/0116877 A1* | 6/2004 | Yang | 604/263 |
| 2005/0171477 A1 | 8/2005 | Rubin et al. | |
| 2006/0229559 A1 | 10/2006 | Marano-Ford et al. | |
| 2007/0017929 A1 | 1/2007 | Bracht | |
| 2007/0049873 A1 | 3/2007 | Hansen et al. | |
| 2008/0039794 A1 | 2/2008 | Kornerup et al. | |
| 2008/0051715 A1 | 2/2008 | Young et al. | |
| 2008/0097324 A1 | 4/2008 | Adams et al. | |
| 2008/0214995 A1 | 9/2008 | Boyd et al. | |
| 2008/0269683 A1 | 10/2008 | Bikovsky | |
| 2008/0306436 A1 | 12/2008 | Edwards et al. | |
| 2009/0082727 A1 | 3/2009 | Moeller et al. | |
| 2009/0204071 A1* | 8/2009 | Grant et al. | 604/113 |
| 2009/0254060 A1 | 10/2009 | Hetherington | |

OTHER PUBLICATIONS

Exhibit B: Co-pending PCT Patent Application No. PCT/US09/65648 filed Nov. 24, 2009. (not prior art but being cited in the interest of full disclosure).

Exhibit C: Co-pending PCT Patent Application No. PCT/US09/65652 filed Nov. 24, 2009. (not prior art but being cited in the interest of full disclosure).

* cited by examiner

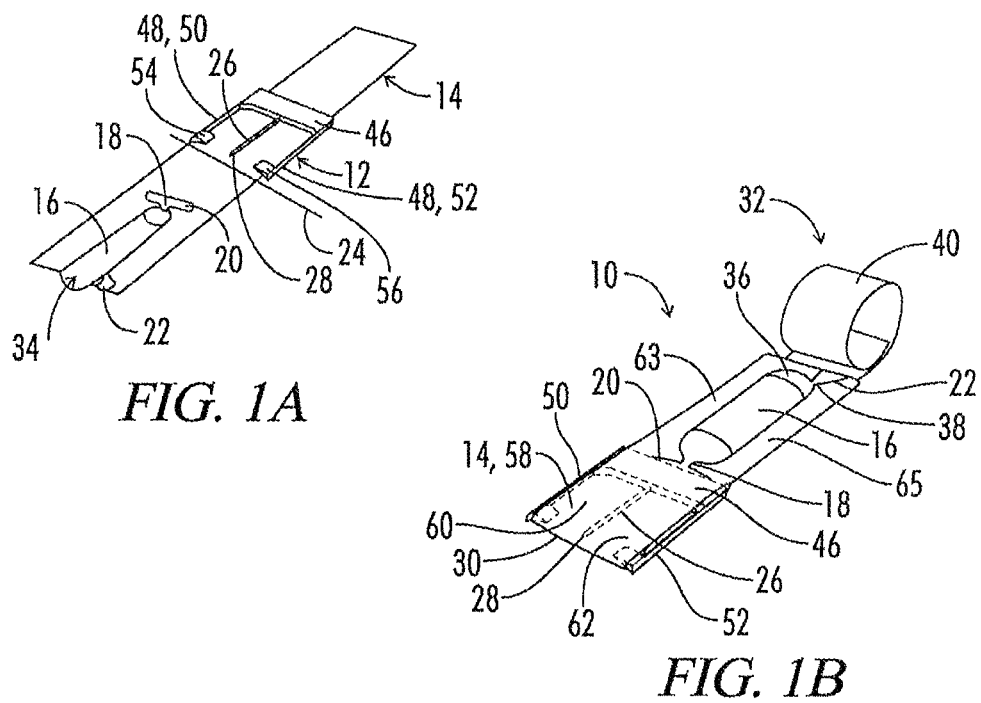
FIG. 1A
FIG. 1B
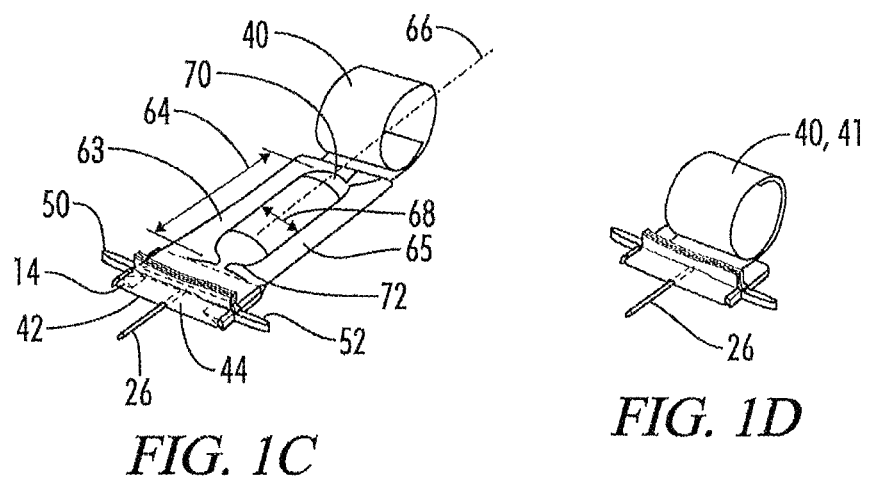
FIG. 1C
FIG. 1D

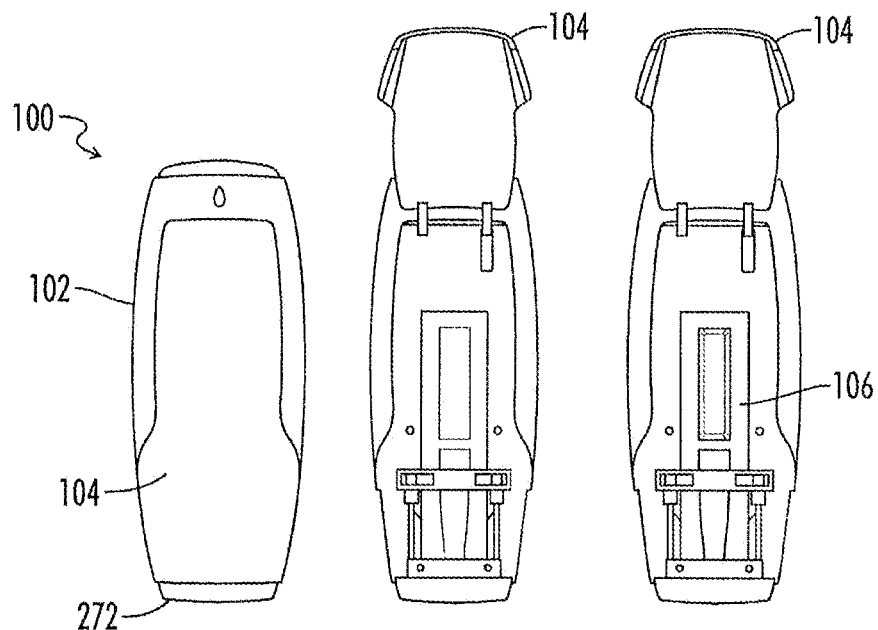
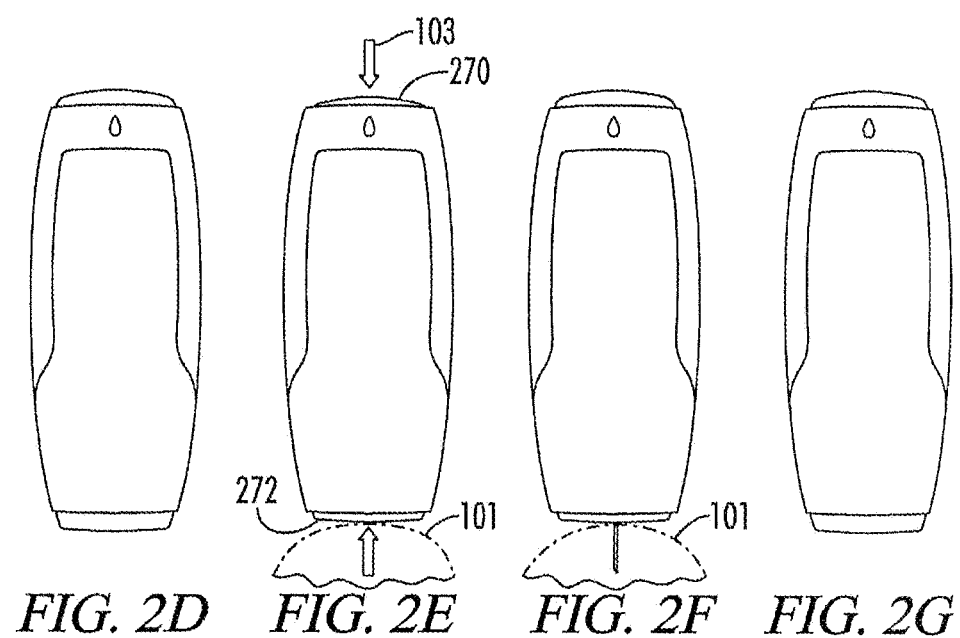
FIG. 2A  FIG. 2B  FIG. 2C
FIG. 2D  FIG. 2E  FIG. 2F  FIG. 2G

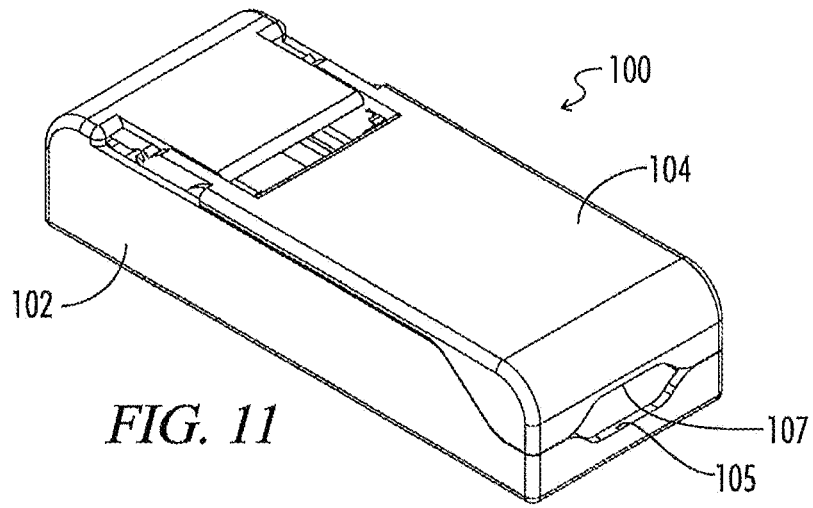
FIG. 11
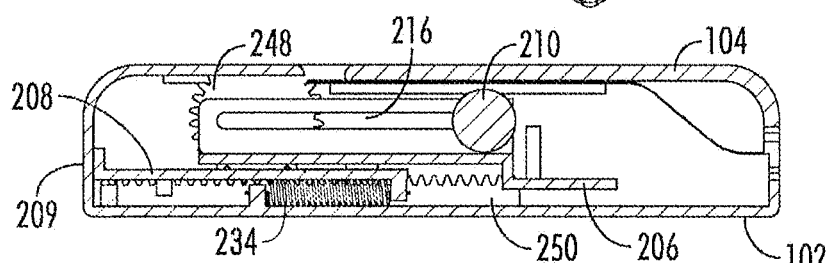
FIG. 12 B-B
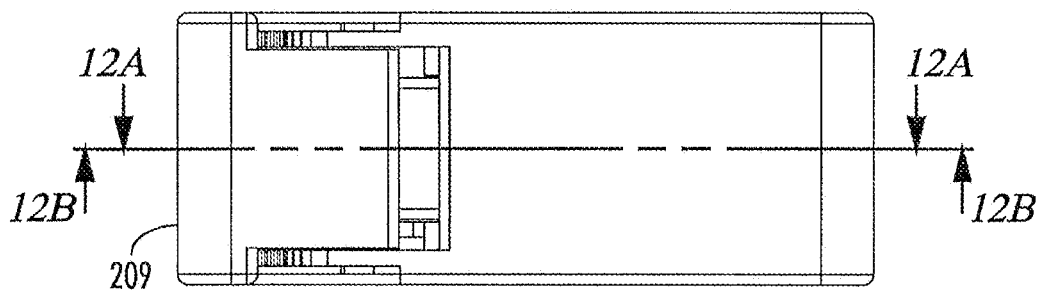
FIG. 12
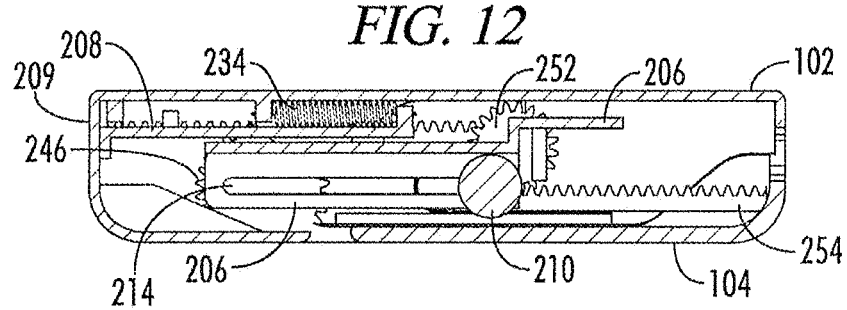
FIG. 12 A-A

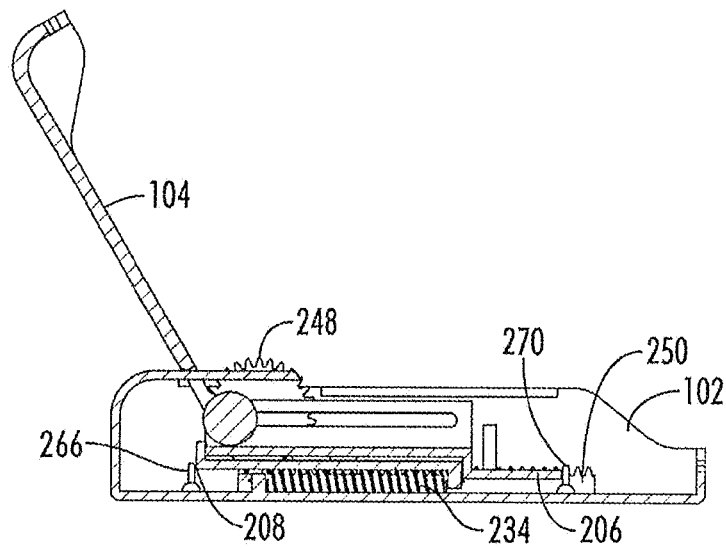
FIG. 14 B-B
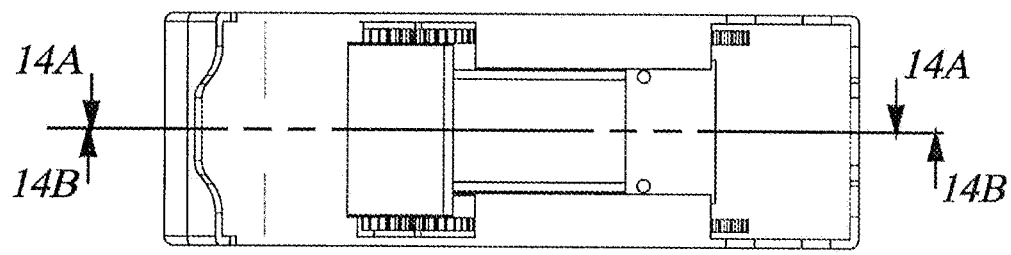
FIG. 14
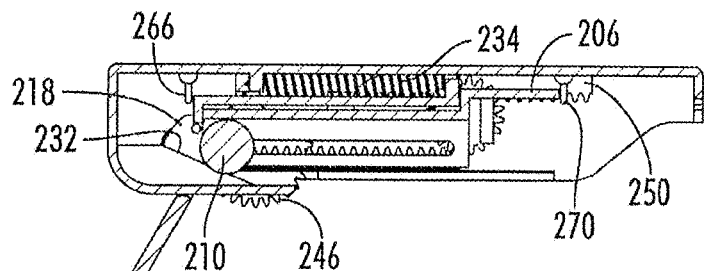
FIG. 14 A-A

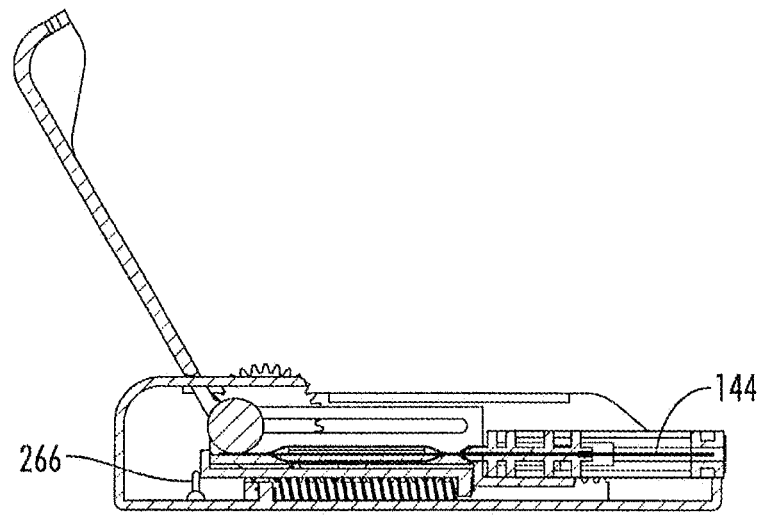
FIG. 16 B-B
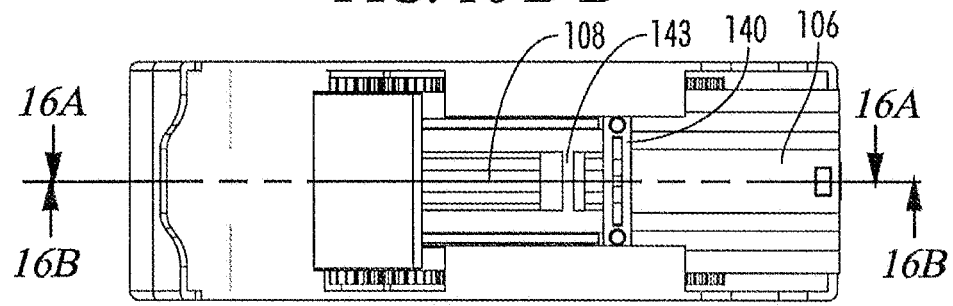
FIG. 16
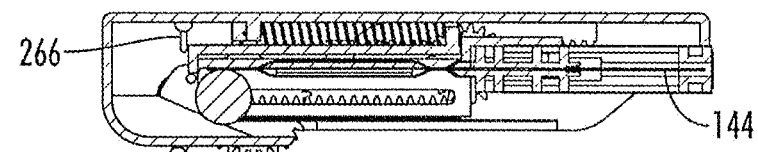
FIG. 16 A-A

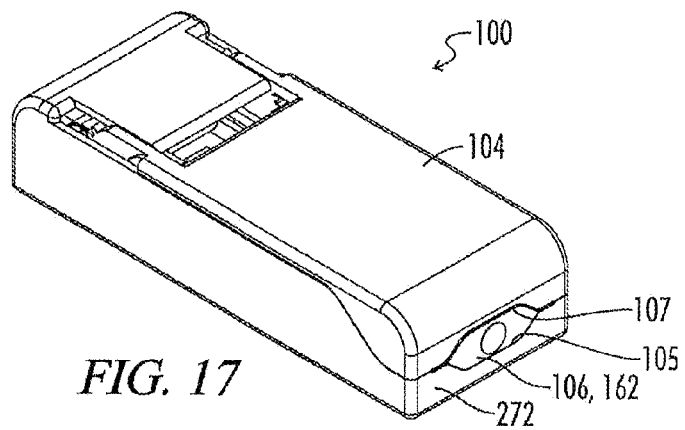
FIG. 17
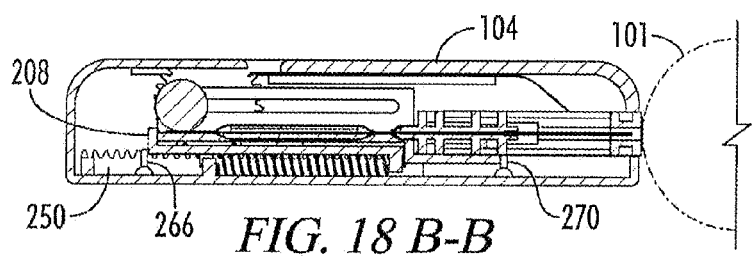
FIG. 18 B-B
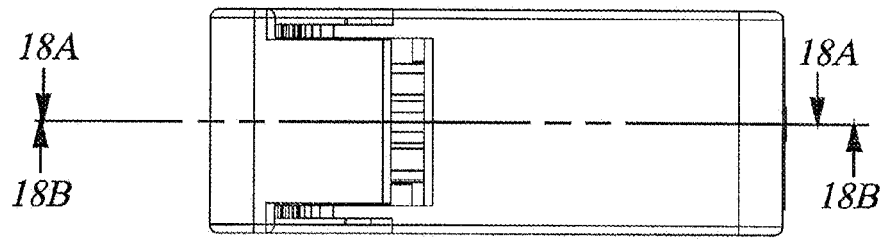
FIG. 18
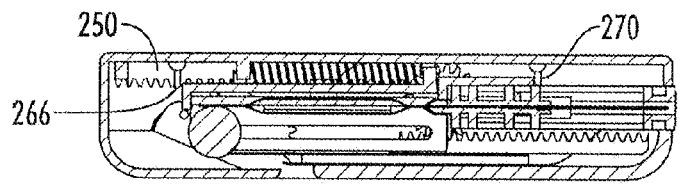
FIG. 18 A-A

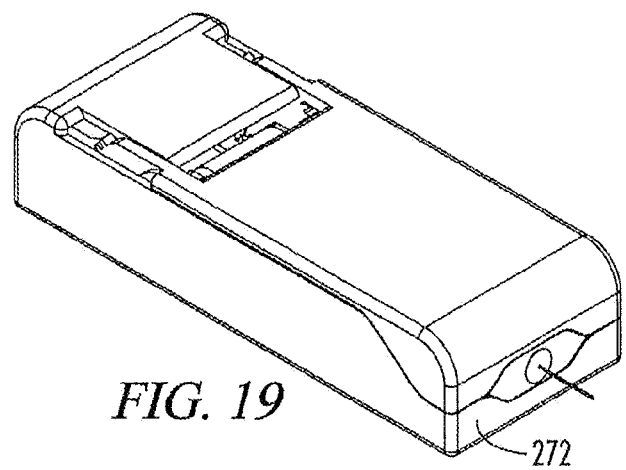
FIG. 19
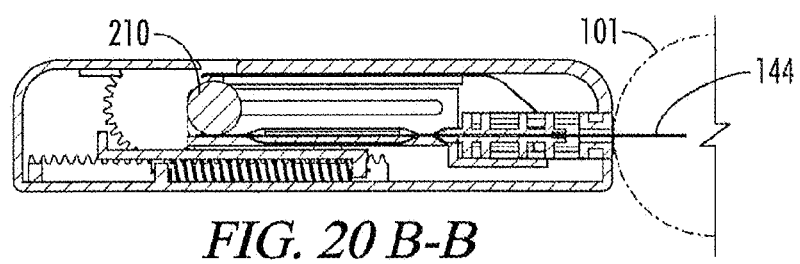
FIG. 20 B-B
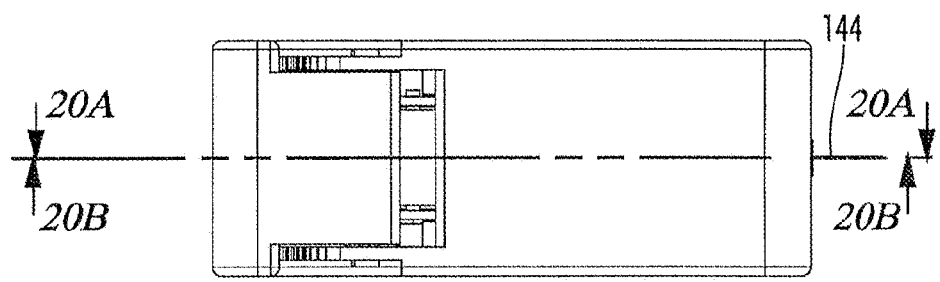
FIG. 20
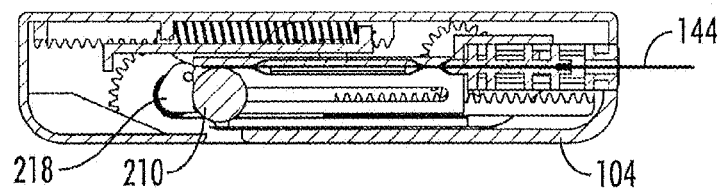
FIG. 20 A-A

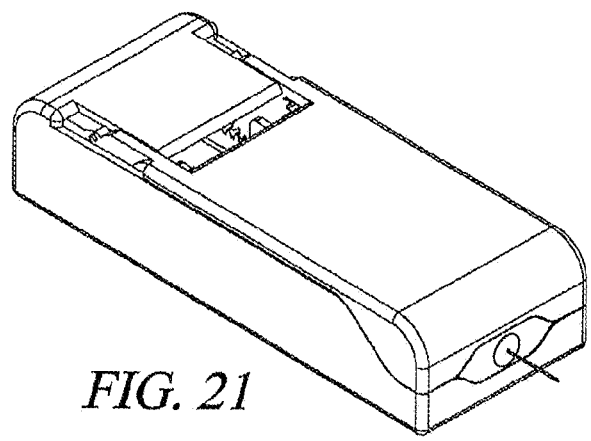
*FIG. 21*
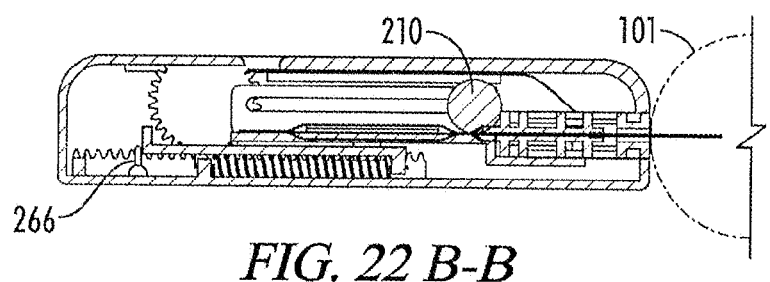
*FIG. 22 B-B*
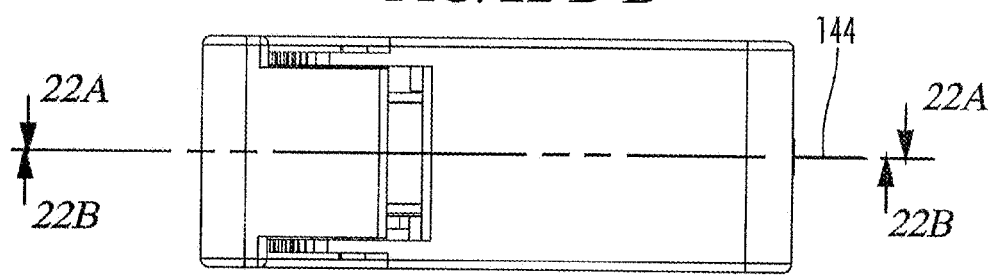
*FIG. 22*
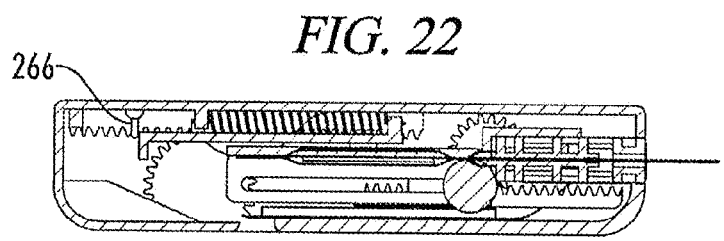
*FIG. 22 A-A*

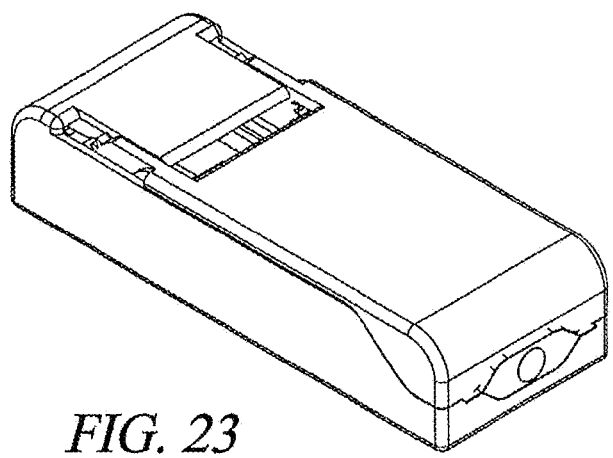
FIG. 23
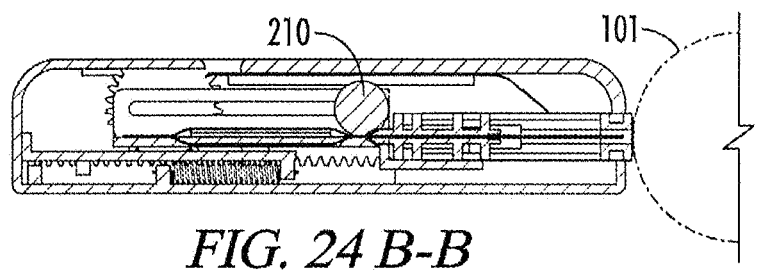
FIG. 24 B-B
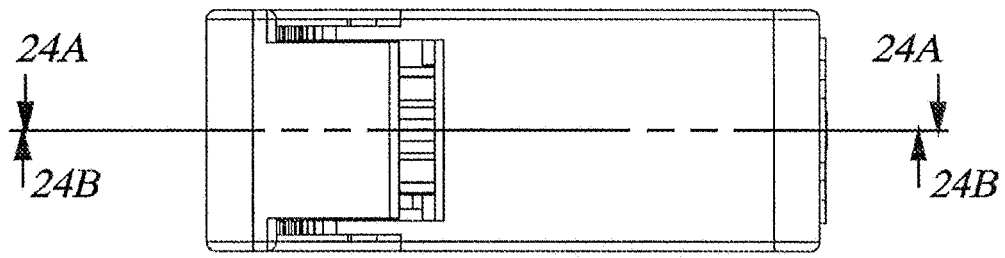
FIG. 24
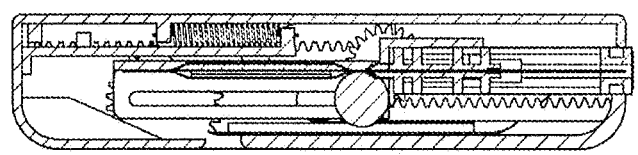
FIG. 24 A-A

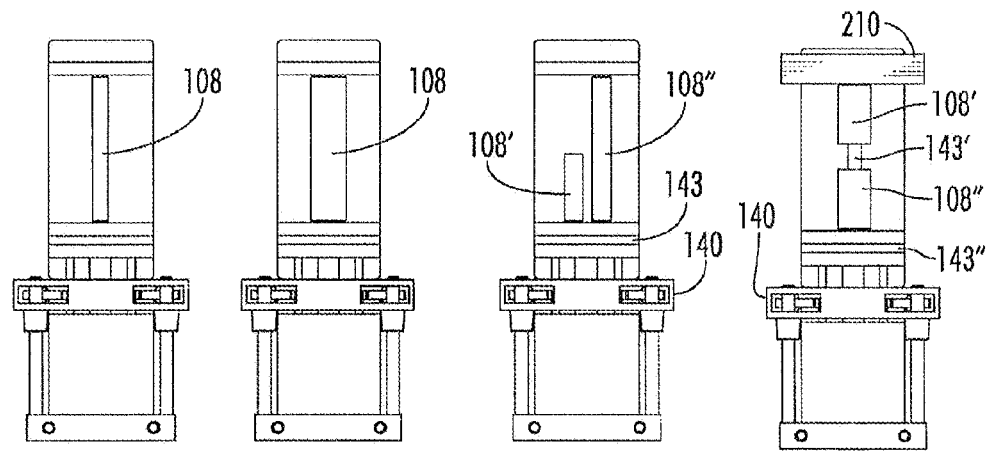
*FIG. 26A*  *FIG. 26B*  *FIG. 26C*  *FIG. 26D*
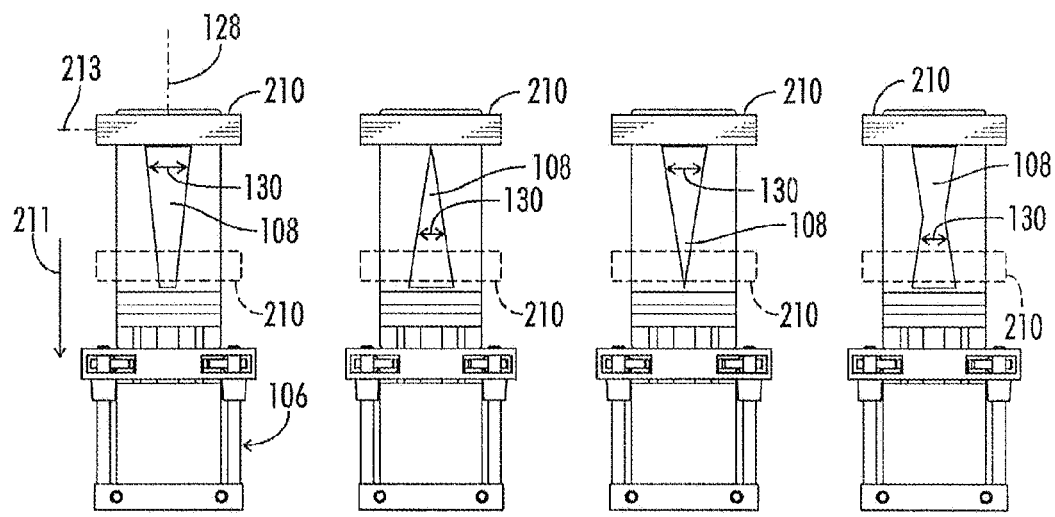
*FIG. 26E*  *FIG. 26F*  *FIG. 26G*  *FIG. 26H*

US 8,690,836 B2

AUTO-INJECTOR APPARATUS

This application claims priority from United Kingdom Patent Application No. 0821492.6 for "Integrated Auto-Injector Cartridge" filed on Nov. 25, 2008.

BACKGROUND OF THE INVENTION

1. Field of the Invention

The present invention relates generally to auto-injector apparatus for injecting medicants into a patient.

2. Description of the Prior Art

To aid convenience in injecting drugs it is desirable to simplify the process by inserting the needle into the delivery site, delivering the drug and subsequently sheathing the needle with minimal user input. The prior art has included a number of auto-injector devices for performing this process. Most prior art auto-injectors use glass based syringes or cartridges as the primary packaging for the drug or medicant.

There is a continuing need for improved auto-injector apparatus that are simple and reliable in their use and economical in their manufacture.

SUMMARY OF THE INVENTION

In one aspect an auto-injector apparatus includes a flexible container containing a liquid medicant, a needle communicated with the flexible container, a housing with the container being received in the housing, a pump disposed in the housing and positioned to engage the flexible container and expel the medicant from the container through the needle upon relative movement between the pump and the container, and a main drive spring operably associated with the needle to extend the needle from a first needle position wherein the needle is completely received in the housing to the second needle position wherein the needle protrudes from the housing. The pump may include a roller.

In a second aspect a method of auto-injecting a liquid medicant into a patient includes placing a proximal end of an auto-injector apparatus against the patient's body, releasing a main spring, driving a needle proximally within the apparatus with the main drive spring so that the needle extends out of the proximal end of the apparatus thereby inserting the needle in the patient's body, and creating relative motion between a pump and a flexible medicant container within the apparatus and thereby forcing the medicant out of the flexible container through the needle into the patient's body. The pump may include a roller.

In another aspect an auto-injector apparatus includes a flexible container containing a liquid medicant, a needle communicated with the container, and a roller positioned to engage the flexible container and expel the medicant from the container upon relative movement in a displacement direction between the roller and the container, wherein the flexible container has a width transverse to the displacement direction and the width varies along the displacement direction.

Numerous objects, features, and advantages of the present invention will be readily apparent to those skilled in the art upon a reading of the following disclosure when taken in conjunction with the accompanying drawings.

BRIEF DESCRIPTION OF THE DRAWINGS

FIGS. 1A-1D comprise a schematic series of figures illustrating the manufacture and the use of an embodiment of the auto-injector apparatus.

FIG. 1A illustrates the manufacture of the embodiment of FIGS. 1A-1D.

FIG. 1B illustrates the embodiment of FIGS. 1A-1D ready for use.

FIG. 1C illustrates an intermediate step in the use of the embodiment of FIGS. 1A-1D wherein the needle has been uncovered as it would during insertion into a patient's body.

FIG. 1D illustrates a further stage in the use of the embodiment of FIGS. 1A-1D wherein a coil strip spring has rolled over the flexible cartridge to inject the medicant.

FIGS. 2A-2G comprise a sequential series of illustrations of the steps of usage of an auto-injector apparatus having an injector device using replaceable cartridges.

FIG. 2A shows the device after usage and ready for reloading.

FIG. 2B shows the device opened for removal of the spent cartridge.

FIG. 2C shows a replacement cartridge in place within the device.

FIG. 2D shows the device closed and ready for use.

FIG. 2E shows the device as it would appear with its proximal end engaged against the patient's body and with a trigger on its distal end depressed.

FIG. 2F illustrates the device with the needle extended from the device as it would appear during insertion into the patient's body and injection of the medicant.

FIG. 2G shows the device with the needle withdrawn and back in the same condition as FIG. 2A.

FIG. 8A shows a perspective view of the apparatus of FIG. 3 ready for use.

FIG. 8B shows a perspective view of the apparatus of FIG. 3 wherein a needle protection frame is shown in a collapsed position with the needle extended therefrom for insertion into the patient and injection of a medicant.

FIG. 9A shows the interlock in a locked position prior to closure of the lid of the device.

FIG. 9B illustrates with downward vertical arrows the application of downward force as would occur by two pins (not shown) of the lid upon closure.

FIG. 9C shows the collapsed position of the needle protection frame with the frame arms sliding through the needle hub.

FIGS. 11, 13, 15, 17, 19, 21 and 23 comprise a sequential series of perspective views of the apparatus of FIG. 10 showing a series of steps in the use of the apparatus.

FIG. 11 is a perspective view of the apparatus of FIG. 10 in a first position prior to opening of the device and prior to loading a cartridge in the device.

FIG. 12 is a plan view of the apparatus of FIG. 11.

FIG. 12A-A is an elevation section view of the apparatus of FIG. 12 taken along line A-A.

FIG. 12B-B is an elevation section view of the apparatus of FIG. 12 taken along line B-B.

FIG. 13 is a perspective view of the apparatus of FIG. 10 in a second position wherein the lid has been opened and prior to placement of a cartridge in the device.

FIG. 14 is a plan view of the apparatus of FIG. 13.

FIG. 14A-A is an elevation section view of the apparatus of FIG. 14 taken along line A-A.

FIG. 14B-B is an elevation section view of the apparatus of FIG. 14 taken along line B-B.

FIG. 15 is a perspective view of the apparatus of FIG. 10 in a third position with a cartridge having been placed within the device.

FIG. 16 is a plan view of the apparatus of FIG. 15.

FIG. 16A-A is an elevation section view of the apparatus of FIG. 16 taken along line A-A.

FIG. 16B-B is an elevation section view of the apparatus of FIG. 16 taken along line B-B.

FIG. 17 is a perspective view of the apparatus of FIG. 10 in a fourth position with the cartridge in place and with the lid closed.

FIG. 18 is a plan view of the apparatus of FIG. 17.

FIG. 18A-A is an elevation section view of the apparatus of FIG. 18 taken along line A-A.

FIG. 18B-B is an elevation section view of the apparatus of FIG. 18 taken along line B-B.

FIG. 19 is a perspective view of the apparatus of FIG. 10 in a fifth position wherein the needle is protruding from the device as it would upon insertion into a patient's body, but prior to injection of the medicant into the patient.

FIG. 20 is a plan view of the apparatus of FIG. 19.

FIG. 20A-A is an elevation section view of the apparatus of FIG. 20 taken along line A-A.

FIG. 20B-B is an elevation section view of the apparatus of FIG. 20 taken along line B-B.

FIG. 21 is a perspective view of the apparatus of FIG. 10 in a sixth position after the medicant has been injected into the patient. It is noted that FIG. 21 appears the same as FIG. 19, but the positions of the internal components have changed.

FIG. 22 is a plan view of the device of FIG. 21.

FIG. 22A-A is an elevation section view of the apparatus of FIG. 22 taken along line A-A.

FIG. 22B-B is an elevation section view of the apparatus of FIG. 22 taken along line B-B.

FIG. 23 is a perspective view of the embodiment of FIG. 10 in a seventh position wherein the needle has been withdrawn back into the device.

FIG. 24 is a plan view of the device of FIG. 23.

FIG. 24A-A is an elevation section view of the apparatus of FIG. 24 taken along line A-A.

FIG. 24B-B is an elevation section view of the apparatus of FIG. 24 taken along line B-B.

FIGS. 26A-26H illustrate several variations on the size and shape of the flexible drug container. FIG. 26A shows a container of relatively low volume. FIG. 26B shows a container of relatively high volume. FIG. 26C shows dual parallel containers which allow two drugs to be mixed during injection. FIG. 26D shows dual containers in series which allow two drug components to be mixed during injection. FIGS. 26E-H show several variations of a profiled container which affects the rate of delivery of medicant.

DETAILED DESCRIPTION OF THE PREFERRED EMBODIMENTS

The Embodiment of FIGS. 1A-1D

Figure 3:
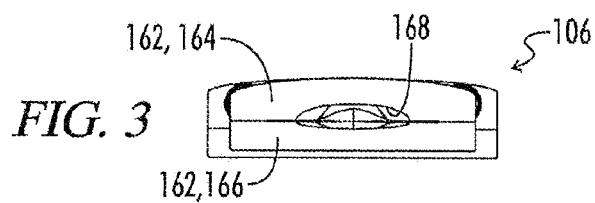
FIG. 3 is an end view of an embodiment of a replaceable cartridge for an auto-injector apparatus.

FIGS. 1A-1D schematically illustrate one embodiment of an auto-injector apparatus.

FIG. 1A schematically illustrates a step in the assembly of an auto-injector apparatus 10, a more complete assembly of which is shown in FIG. 1B. In FIG. 1A, a needle sub-assembly 12 is laid in place upon a flat portion of a flexible substrate 14.

The flexible substrate 14 begins as a flat flexible sheet of material which may for example be a polymer material and may include a laminated metal layer as further described below. A drug containment volume 16, which may also be referred to as a flexible container 16, has been formed in a blister manner into the flat flexible sheet. Also formed into the sheet are a necked down passage 18, a manifold portion 20, and a bleed vent 22.

In FIG. 1B, the substrate 14 has been folded over about a fold line 24 and the flat portions of the flexible substrate have been sealed together where they engage. Also, the necked down passage 18, which may also be referred to as neck 18, has been sealed to isolate needle 26 and close the drug containment volume 16 at its proximal end.

It is noted that in this description, the term "proximal" is used to refer to the end of the apparatus that is closest to or engaged with the patient when the apparatus is in use to inject the medicant into the patient's body. Thus the sharp end 28 of the needle 26 is referred to as the proximal end of needle 26. Similarly, the proximal end of the apparatus 10 is indicated at 30. Accordingly the distal end of the apparatus 10 is indicated at 32.

After the substrate 14 has been folded over and the flat portions and the neck 18 have been sealed, the drug containment volume 16 is filled with a drug or medicant which is placed through the top end 34 of the still open drug containment volume 16, then the top end is closed or sealed as indicated at 36 in FIG. 1B.

Then, the volume of the drug containment volume 16 is compressed slightly to expel residual air through the bleed feature 22 after which a neck 38 of the bleed feature 22 is sealed to completely seal the drug containment volume 16.

Then the back side of the substrate 14 adjacent the drug containment volume 16 is bonded to an unrolled coil spring strip 40 also sometimes referred to as a Tensator spring 40.

FIGS. 1C and 1D schematically illustrate two steps in the use of the apparatus 10. In FIG. 1C, the actuation of the apparatus 10 has begun, and the drug containment volume 16 and needle sub-assembly 12 including needle 26 have moved axially forward in a proximal direction forcing the needle 26 to protrude through the front 42 of the substrate material 14 with excess material bunching as indicated at 44 near the root of the needle 26. It will be understood that this step in the actuation, and the proximal movement of the drug containment volume and needle sub-assembly 12 is accomplished by means of an actuating mechanism which is not shown in FIGS. 1A-1D.

In FIG. 1D, the coil spring strip 40 has been released and has rolled forward proximally into its natural coiled state. As the loop of the coil spring strip 40 rolls forward, it compresses the flexible drug containment volume 16 and expresses the drug contained therein through the passage 18 and through the needle 26 into the patient. The loop may be described as an integral roller portion 41 of the coil spring strip 40.

Several features are provided by the integrated assembly of the apparatus 10 shown in FIGS. 1A-1D.

The apparatus 10 provides drug containment in the flexible container defined by the drug containment volume 16 and the surrounding flexible substrate 14.

The properties of the material selected for the substrate 14 which forms the flexible barrier around the drug containment volume 16 may be selected as appropriate.

The folded substrate material about the needle sub-assembly 12 as seen in FIG. 1D provides needle sterility until the point of use of the apparatus 10.

The frangible seal provided at neck 18 provides a dry needle in storage.

The bleed feature 22 provides a means of air removal during filling.

The potential is provided for having two of the drug compartments 16 formed in the substrate 14 which provides a lyophilized powder option, as is for example further discussed below with regard to FIG. 26D.

The apparatus 10 allows for flexible fill volumes by selection of the size of the drug containment volume 16 formed in the substrate 14.

The use of a roller to express the drug from the flexible volume 16 allows full delivery of contents from the volume 16 through the needle 26.

The apparatus 10 is compact in size and relatively low in cost.

The apparatus 10 aids convenience in injecting drugs by simplifying the drug injection process by inserting the needle into the delivery site, delivering the drug and subsequently sheathing the needle with minimal user input.

As best seen in FIG. 1A, the needle sub-assembly 12 includes a needle hub 46 which as shown in FIG. 1B is structurally connected to the flexible container 16 via the folded layers of the substrate 14, and is fluidly connected to the interior of container 16 via the passage 18 and the manifold portion 20 which communicate with an opening (not shown) in the needle hub 46 which in turn communicates with the needle 26.

The needle 26 is attached to the needle hub 46 and extends proximally from the needle hub 46. A needle protection frame 48 is connected to the needle hub 46. The frame 48 includes first and second transversely spaced frame arms 50 and 52 which are supported from the needle hub 46 on opposite sides of the needle 26 and extend proximally beyond the proximal end 28 of needle 26. Laterally inward extending supports 54 and 56 are defined on the proximal ends of arms 50 and 52, respectively, to aid in supporting the folded over substrate 14 as seen in FIG. 1B. The arms 50 and 52 hold the front 42 of substrate material 14 away from proximal end 28 of needle 26.

When the container 16, needle hub 46 and needle 26 move proximally forward from the position of FIG. 1B to the position of FIG. 1C relative to the front 42 of laminated substrate 14, the frame arms 50 and 52 fold up in an accordion like manner as shown in FIG. 1C to allow the relative movement between needle 26 and the front 42 of the laminate 14. The needle hub 46 and the needle 26 may be described as being displaceable relative to the frame 48 in a proximal direction to insert the needle 26 into a patient.

Those portions of the laminated material 14 folded over the needle 26 between the arms 50 and 52 as seen in FIG. 1B may be referred to as a flexible needle pouch 58 connected to the frame 48 and covering the needle 26 to maintain the needle 26 in a sterile condition prior to use. As illustrated, the pouch 58 is collapsible so that the needle 26 can protrude through the pouch 58 upon proximal displacement of the needle hub 46 and needle 26 relative to the frame 48.

The two sheets of the substrate 14 forming the needle pouch 58 can be described as a sheet of flexible material 14 folded at fold 24 into two sheet portions joined together along at least two sides as indicated at 60 and 62, the two sides 60 and 62 extending generally parallel to the needle 26 which may be described as being transverse to the fold 24.

The flexible container 16 may be described as being made up of first and second layers of the flexible substrate material 14 joined together to define a container space 16 therebetween, the first and second layers of the substrate 14 further defining the passages 18 and 20 communicating the container space 16 with the needle hub 46.

As previously noted, the necked down portion 18 of the passage is temporarily closed to provide a frangible seal temporarily closing the passage 18 to isolate the needle 26 from medicant in the volume 16. That frangible seal is formed by joining portions of the first and second layers of the substrate 14 so that they are lightly sealed together across the passage 18 thus blocking the passage 18 until the pressure within the container 16 is sufficient to break that seal across the neck down portion 18 by causing the two layers to peel away from each other.

The flexible container 16 may also be described as comprising first and second layers of the flexible substrate 14, which may be described as a flexible film 14, joined together around at least part of a containment perimeter so that the interior volume of container 16 is a containment space defined between unjoined portions of the first and second layers of the substrate 14. As is apparent in FIGS. 1B and 1C, the container or containment space 16 is an elongated space having a length 64 extending generally parallel to a proximal/distal axis 66 of the container 16, and having a width 68 transverse to and less than the length 64, so that the containment space 16 has two lengthwise sides 63 and 65 parallel to length 64, a distal side 70 and a proximal side 72. The first and second layers of the substrate material 14 are joined together on at least the two lengthwise sides 63 and 65 and the distal side 70, and the two layers of substrate 14 are further joined together to define the passages 18 and 20 communicating the proximal side 72 of the containment space 16 with the needle hub 46.

The coil spring strip 40 may be described as a drive spring 40 having its integral roller portion 41 which rolls over the flexible container 16 after the needle 26 is extended to the position shown in FIGS. 1C and 1D.

The Embodiment of the Multi-Use Apparatus of FIGS. 2-24

FIGS. 2A-2G comprise a sequential series of illustrations showing the manner of usage of a multi-use auto-injector apparatus which is generally designated by the numeral 100. The apparatus 100 includes a housing 102 having a lid 104 which may be opened as indicated in FIGS. 2B and 2C to allow removal and replacement of a cartridge assembly 106.

The Cartridge Assembly

Figure 4:
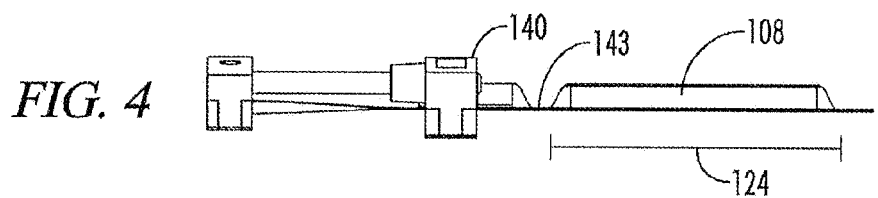
FIG. 4 is a right side elevation view of the apparatus of FIG. 3.
Figure 5:
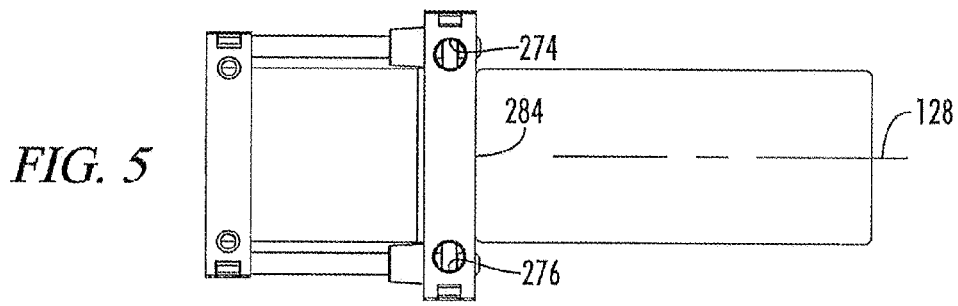
FIG. 5 is a bottom view of the apparatus of FIG. 3.
Figure 6:
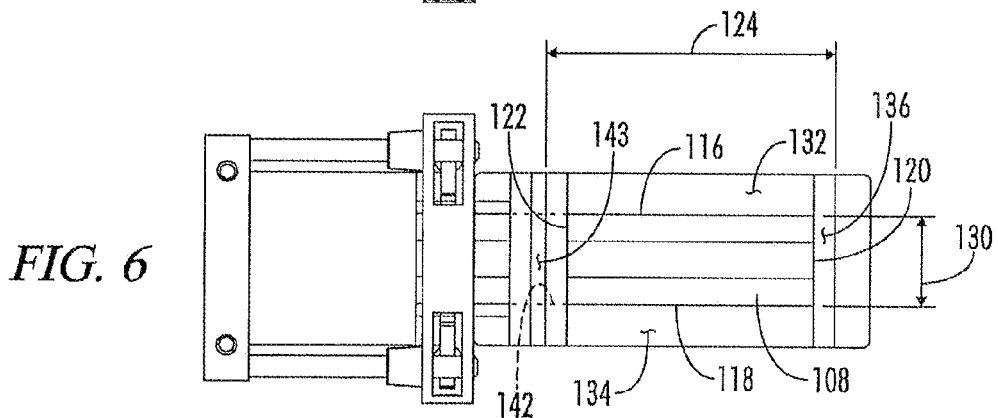
FIG. 6 is a top plan view of the apparatus of FIG. 3.
Figure 7:
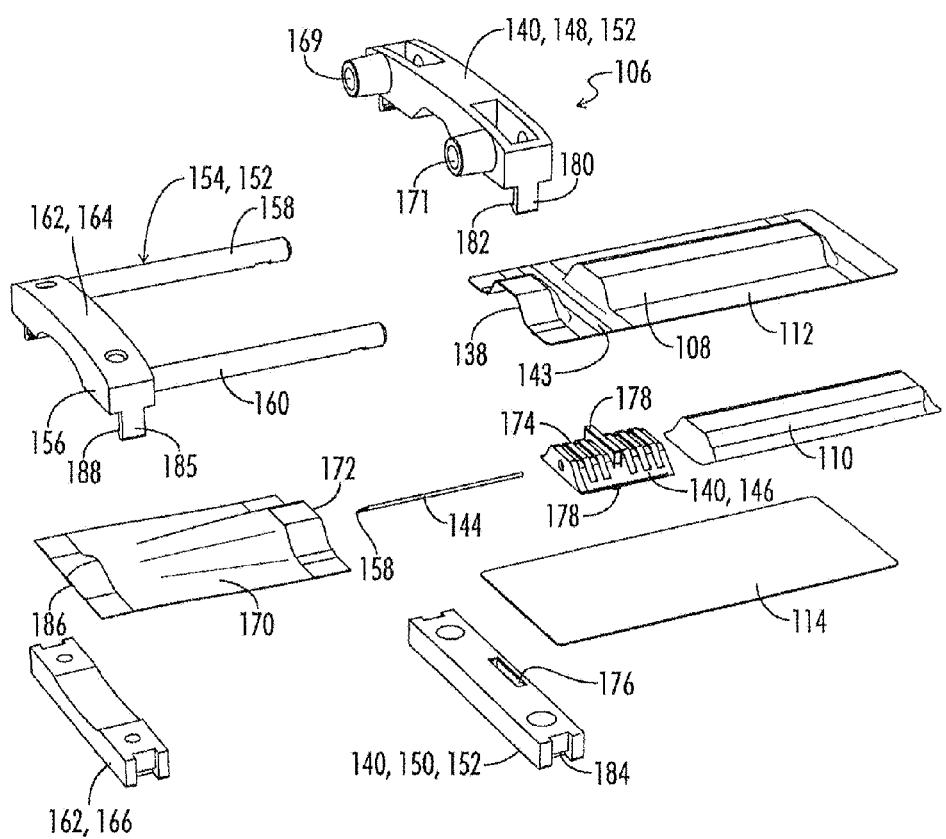
FIG. 7 is a perspective exploded view of the apparatus of FIG. 3.

The details of construction of the cartridge assembly 106 are seen in FIGS. 3-9. FIG. 3 is a proximal end view of the cartridge assembly 106. FIG. 4 is a right side elevation view of the cartridge assembly 106. FIG. 5 is a bottom view of the cartridge assembly 106. FIG. 6 is a top plan view of the cartridge assembly 106. FIG. 7 is a perspective exploded view showing the components of the cartridge assembly 106. FIGS. 8A and 8B show the cartridge assembly in two different operating positions.

The cartridge assembly 106 includes a flexible container 108 that as schematically illustrated in FIG. 7 includes a liquid medicant 110. As best seen in FIG. 7, the flexible container 108 comprises first and second layers 112 and 114 of flexible film joined together. As shown in FIG. 6, the layers 112 and 114 of film are joined together around at least a part of a containment perimeter defined by two lengthwise sides 116 and 118, a distal side 120 and a proximal side 122. The interior of flexible container 108 may be described as a containment space which is defined between unjoined portions of the first and second layers 112 and 114. That containment space is an elongated space having a length 124 extending generally parallel to a proximal/distal axis 128 of the container 108, and having a width 130 transverse to and less than the length 124, so that the containment space within container 108 has the two lengthwise sides 116 and 118 mentioned plus the distal side 120 and the proximal side 122.

The first and second layers 112 and 114 are joined together along the two lengthwise sides 116 and 118 in the areas as indicated at 132 and 134, and along the distal side 122 in the area as indicated at 136.

The upper layer of film 112 has a manifold portion 138 formed therein as best seen in FIG. 7. The manifold portion 138 is shaped so as to closely fit over a distal portion of a central hub portion 146 of a needle hub 140. The needle hub 140 includes the central hub portion 146 and upper and lower hub clamps 148 and 150. The upper and lower hub clamp portions 148 and 150 have slots such as 176 therein for receiving positioning ribs such as 178 of central hub 146 therein. The upper and lower clamp portions 148 and 150 are held together by flexible arms such as 180 having laterally inward extending protrusions such as 182 which snap fit below ledges such as 184 on the lower clamp part 150.

As generally indicated by the dotted line 142 in FIG. 6, a passage 142 communicates the interior of the container 108 with the manifold portion 138 and thus with the needle hub 140. After the container space within the flexible container 108 has been filled with the medicant 110, the passage 142 is temporarily sealed by a frangible seal 143 which is formed by pressing the first and second layers 112 and 114 of flexible film together and lightly sealing the two together across the passage 142 so as to temporarily seal the medicant within the flexible container 108. As is further described below, during use of the apparatus 106 a roller will roll across the flexible container 108 from its distal end 120 toward its proximal end 122 and the pressure within the flexible container 108 will break the seal 143 by causing the layers 112 and 114 to peel apart within the area of the passage 142 thus allowing the liquid medicant to flow from the container 108 through the passage 142 and through the central hub portion 146 of needle hub 140 to a needle 144.

The hub 140 and needle 144 are part of a needle subassembly 152 which further includes a needle protection frame 154 connected to the needle hub 140 and including a frame proximal end 156 extending proximally beyond a proximal end 158 of needle 144. As is apparent in viewing FIGS. 8A and 8B, the needle hub 140 and needle 144 are displaceable relative to the frame 154 in a proximal direction to insert the needle 144 into a patient.

The needle protection frame 154 includes first and second transversely spaced frame arms 158 and 160 supported from the needle hub 140 on opposite sides of the needle 144 and extending proximally beyond the proximal end 158 of needle 144.

The frame 154 further includes a front bar 162 made up of upper and lower front clamp halves 164 and 166, spanning between the proximal ends of the frame arms 158 and 160 to protect the proximal end 158 of the needle 144 when the needle 144 is in an initial position corresponding to FIGS. 4-6 and FIG. 8A. The upper and lower front clamp portions 164 and 166 are held together by flexible arms such as 185 on the upper clamp portion having laterally inward extending protrusion 188. As best seen in FIG. 3, the front bar clamp portions have recesses defined therein which form an opening 168 through the front bar 162 through which the needle 144 passes when the needle moves proximally relative to the frame 154 to insert the needle into a patient. Such proximal movement is illustrated in the position of FIG. 8B wherein the needle 144 has passed through the opening 168.

The upper hub clamp 148 of needle hub 140 includes first and second cylindrical openings 169 and 171 defined therethrough within which are slidably received the cylindrical arms 158 and 160, respectively.

Figure 8A:
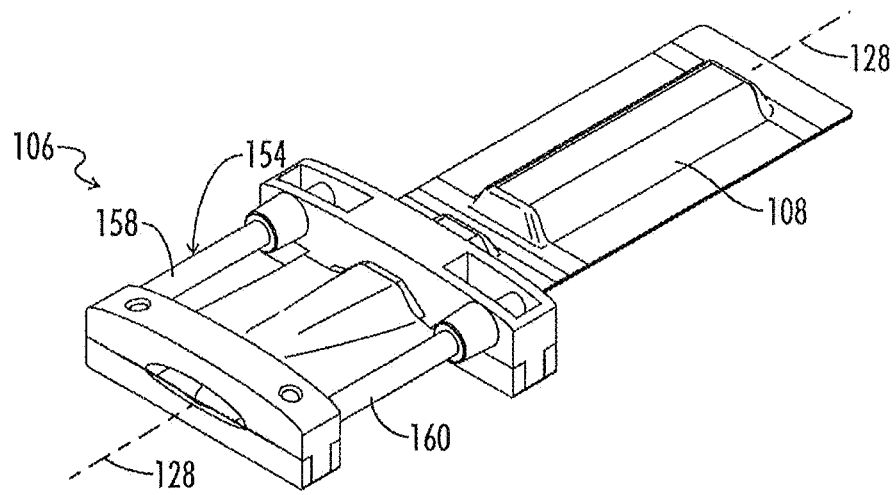
FIGS. 8A-8B comprise a sequential series of perspective views showing the operation of the apparatus of FIG. 3.
Figure 8B:
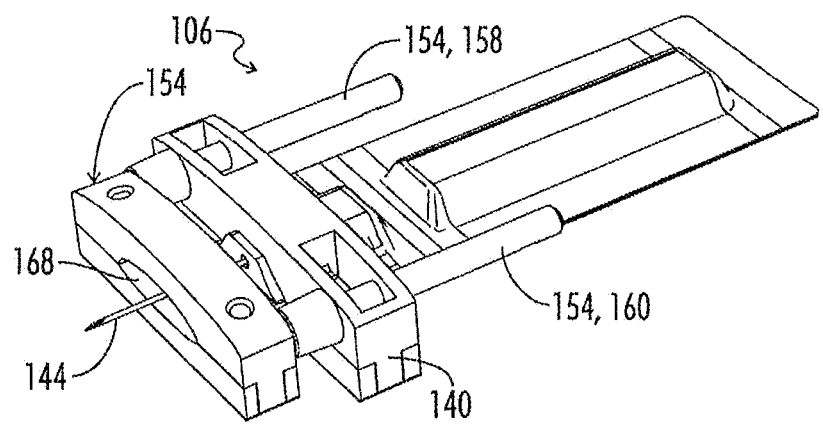

As best seen in comparing FIGS. 8A and 8B, the frame arms 158 and 160 slide through the openings 169 and 171 of needle hub 140 when the needle hub 140 and needle 144 are displaced proximally relative to the frame 154 to insert the needle 144 into a patient.

The needle sub-assembly 152 preferably includes a flexible needle pouch 170 connected to or supported from the frame 154 and covering the needle 144 to maintain the needle 144 in a sterile condition prior to use. The needle pouch 170 is collapsible so that the needle 144 can protrude through the pouch 170 upon proximal displacement of the needle hub 140 and needle 144 relative to the frame 154 as illustrated in FIG. 8B. The flexible needle pouch 170 is preferably formed from two sheets of flexible film in a manner similar to that described for formation of the flexible container 108 from the two sheets 112 and 114. The needle pouch 170 has an opening 172 at a distal end portion that is similar in size and shape to the opening or manifold portion 138 described above, which opening 172 closely fits over a proximal portion 174 of the central hub 146. Needle pouch 170 may be formed from a sheet of flexible material folded at a fold line 186 into two sheet portions joined together along at least two sides transverse to the fold.

The sheets 112 and 114 are preferably joined together by welding of the sheet material. The welding may be accomplished by application of heat, by application of radio frequency energy, by application of ultrasonic energy, by friction welding, or any other suitable welding technique. Alternatively the sheets can be joined by solvent bonding or the use of any other suitable adhesive. The central hub 146 is preferably formed of plastic and is preferably joined to the flexible container 108 and to the needle pouch 170 by welding of the flexible material to the central hub 146.

In any of the embodiments disclosed herein wherein two separate sheets are joined together, such as sheets 112 and 114, an equivalent structure may be provided by folding a single sheet. Similarly, in any of the embodiments disclosed herein wherein a single sheet is folded to form two overlying layers, an equivalent structure may be provided by two separate sheets joined together.

Also, instead of using a needle pouch 170 constructed from two sheets or a folded sheet of flexible material, a formed cylindrical rubber or plastic sheath or nipple may be used and directly attached to needle hub 140.

Figure 9A:
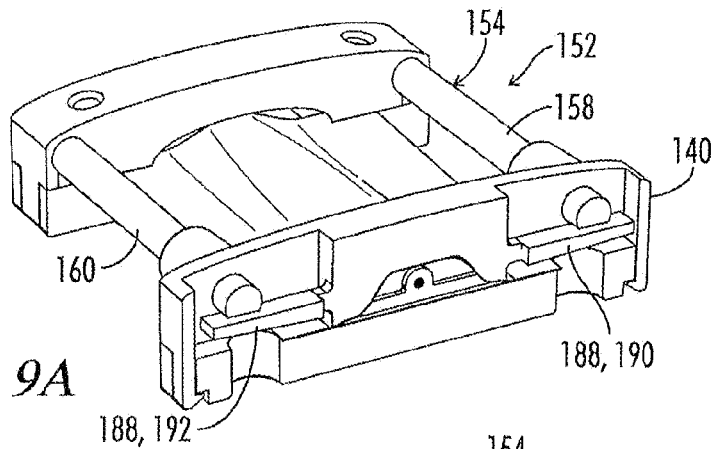
FIGS. 9A-9C comprise a perspective end view of the needle protection frame and needle hub of the apparatus of FIG. 3 illustrating the manner in which a releasable interlock on the needle hub is released upon closure of the lid of the device.
Figure 9B:
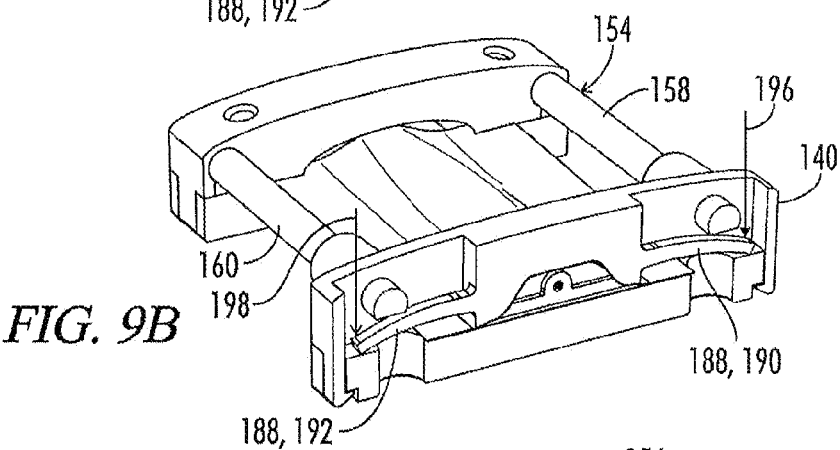
Figure 9C:
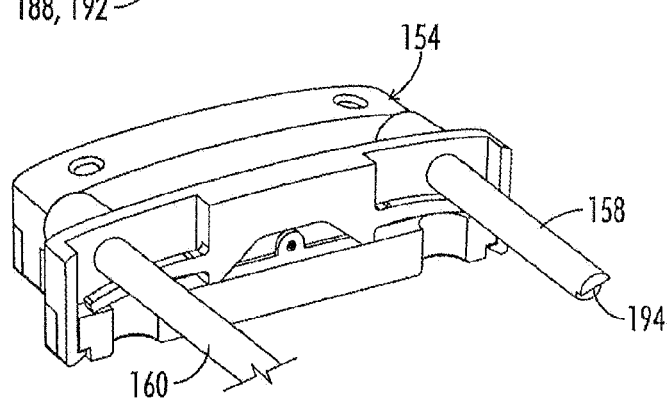

FIGS. 9A-9C illustrate the operation of a releasable lock 188 operably associated with the frame arms 158 and 160 and the needle hub 140. The releasable lock 188 can lock the needle protection frame 154 in the locked position as shown in FIG. 9A wherein the frame arms 158 and 160 are prevented from sliding distally relative to the needle hub 140, and an unlocked position as illustrated in FIGS. 9B and 9C, wherein the needle protection frame 154 is allowed to slide distally relative to the needle hub 140. The releasable lock 188 includes resilient locking arms 190 and 192 which in their unbiased position as shown in FIG. 9A are received in notches such as indicated at 194 in the distal ends of the arms 158 and 160. When the flexible arms 190 and 192 are received in the notches 194 they prevent the arms 158 and 160 from sliding distally through the needle hub 140.

Referring back to the series of FIGS. 2A-2G, when the lid 104 is returned to a closed position as shown in FIG. 2D a pair of pins (not shown) on the underside of the lid 104 engage the flexible arms 190 and 192 and push them downward as indicated by arrows 196 and 198 in FIG. 9B so as to permit the arms 158 and 160 to slide distally as shown in FIG. 9C.

The flexible materials making up the first and second layers 112 and 114 of film which are used to make the flexible container 108 may be selected based upon numerous desirable properties for the flexible container 108. For example, the flexible container 108 may be constructed from a transparent or translucent material so that an extent to which the container 108 is filled with medicant can be observed by the user. Also, the materials from which the container 108 is manufactured may be selected based upon their properties as oxygen and moisture barriers for protection and shelf life of the medicant contained in the container 108. One preferred such material which will be opaque and will provide very high barrier properties is a flexible metallic material which includes an aluminum lamination. Other metallic films, layers or foils could also be used. For example a metallic layer could be vacuum deposited upon an underlying flexible substrate.

Numerous examples of possible flexible materials from which the first and second layers 112 and 114 of film may be selected are set forth in the following Table I along with some approximate properties of these materials as oxygen and moisture barriers. In each case the product is described as a lamination of three materials.

TABLE I

| Product | Total Thickness μm | Oxygen Barrier (1 ml. volume) | | Moisture Barrier (1 ml. volume) | |
|---|---|---|---|---|---|
| | | (g/m²/day) | ppm | (cc/m²/day) | ppm |
| PP/20μ EVOH/PP | 160 | 1.86 | 1897 | 0.2 | 204 |
| PP/40μ EVOH/PP | 160 | 1.93 | 1969 | 0.1 | 102 |
| PP/PET•SIOx/PP | 112 | 0.5 | 510 | 0.5 | 510 |
| PP/23μ PCTFE/PP | 100 | 0.23 | 235 | 120 | 122400 |
| PP/51μ PCTFE/PP | 100 | 0.11 | 112 | 55 | 56100 |
| PP/PET•SIOx/PP (Super) | 112 | 0.001 | 1 | 0.001 | 1 |
| Lacquer/Aluminum/PP | 110 | 0 | 0 | 0 | 0 |

The abbreviations for the products in the first column of Table I refer to the following materials:
1. PP is polypropylene.
2. PCTFE is polychlorotrifluoroethylene. Polychlorotrifluoroethylene is a fluoropolymer that has the best water barrier properties of all suggested polymers. It is also known under the trademark ALCAR®, which is a product of Honeywell.
3. EVOH is ethylene vinyl alcohol. Ethylene vinyl alcohol is a polymer that has outstanding oxygen barrier properties, but is prone to moisture transmission and therefore must be all protected by outer layers.
4. SIOx is silicium oxide. It is a very thin glass layer coated onto a PET film. The coating process can be achieved in many different ways.

The use of a transparent or translucent drug containment film may be suitable for drugs that have low dissolved oxygen and low loss of moisture stability requirements. It has the advantage that visual inspection of the drug at time of manufacture and by the patient before injection is possible. The disadvantage is potential susceptibility to ultraviolet radiation. Many of the polymers listed in Table I may be obtained in a sufficiently transparent form that the level of the liquid medicant in the container can be visualized, although they may not be fully transparent.

For drugs that have higher dissolved oxygen and low loss of moisture stability requirements, an opaque containment film including a foil layer within the film, such as aluminum foil, may be desirable. Such a configuration has the advantage of less susceptibility to ultraviolet radiation. It has the disadvantage that visual inspection of the drug at time of manufacture and by the patient before injection may not be possible.

Figure 35:
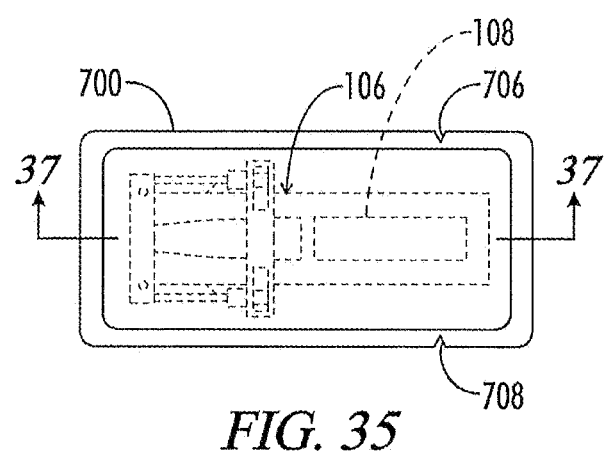
FIG. 35 is a plan view of a cartridge contained in secondary packaging.
Figure 36:
FIG. 36 is a side view of the packaging of FIG. 35.
Figure 37:
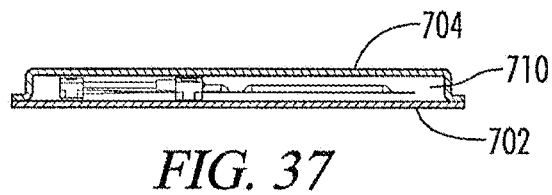
FIG. 37 is a section view taken along line 37-37 of FIG. 35.

External Packaging:

Another option is to utilize a transparent flexible drug containment film which is sealed inside metal foil secondary packaging. This option is suitable for drugs that have high dissolved oxygen and low loss of moisture stability requirements. It has the advantage that visual inspection of the drug at the time of manufacture and by the patient before the injection is possible, and that it is less susceptible to ultraviolet. This solution may also be suitable for drugs that have very high stability requirements, i.e. if the secondary packaging is sealed under nitrogen or contains an oxygen absorbing material. Such an embodiment is shown for example in FIGS. 35-37 wherein the cartridge 106 is shown in place within a foil package 700. The package 700 is made from a bottom layer 702 and a top layer 704 sealed together around their periphery. Top layer 704 is raised as best seen in FIGS. 36 and 37 to create an interior space 710 for storage of the cartridge 106. Notches 706 and 708 are preformed in the package 700 so that it may be torn apart across the width of the package so that the cartridge 106 may be removed for use. The package 700 is preferably made of a metal foil material which will be impermeable to moisture and air. As noted the interior 710 of the package may be sealed under nitrogen or contain an oxygen absorbing material. The flexible container 108 will be made of transparent material so that when it is manufactured, and when it is removed from package 700 for use, it may be visually inspected to insure that it is filled with medicant and that the medicant is clear and contains no particulates.

Figure 38:
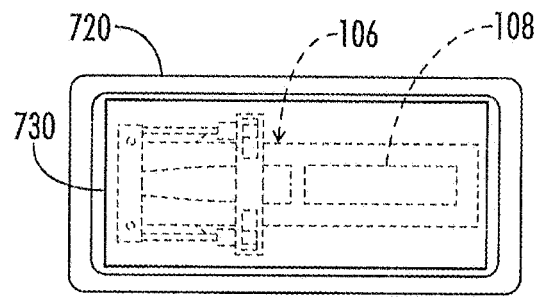
FIG. 38 is a plan view of a cartridge in another embodiment of secondary packaging.
Figure 39:
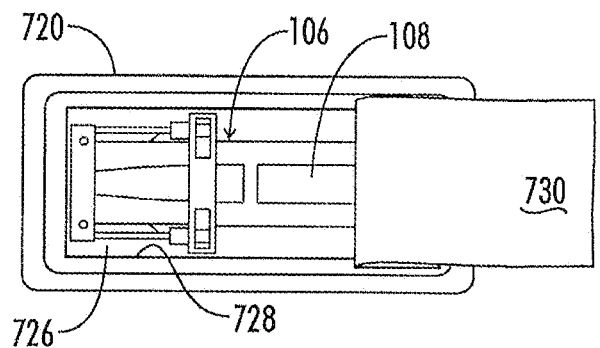
FIG. 39 shows the packaging of FIG. 38 with a cover peeled back.
Figure 40:
FIG. 40 is a side view of the packaging of FIG. 39.

Another form of external packaging is shown in FIGS. 38-40. In this case the cartridge 106 is contained in an opaque package 720, which again is preferably constructed from a metal foil material such as aluminum. Package 720 is made from a bottom layer 702 and a top layer 724 joined around their periphery to define an interior 726. A window 728 is defined in top layer 724 and is initially covered by a peelable strip 730 as shown in FIG. 38. As shown in FIGS. 39 and 40 the strip 730 is peeled back so that the cartridge 106 is visible and can be removed from the packaging. Alternatively the entire top layer can be designed to be peeled back from the bottom layer.

Both of the packaging embodiments 700 and 720 just described are intended for packaging of cartridges for use in multi-use injector devices as further described below. Other external packaging arrangements for single use injector devices are described below with regard to FIGS. 41-43.

Container Shapes:

The shape and dimensions of the flexible container 108 may be selected based upon various considerations. Several alternatives are shown in FIGS. 26A-26H, and it will be understood that due to the design flexibility provided by the use of molding the flexible film to construct the flexible container 108, any desired shape can be readily formed and utilized with the apparatus 100.

For example, FIGS. 26A and 26B show how the volume of liquid medicant contained in the flexible container 108 may be readily changed simply by forming the container 108 to have a smaller volume. The container 108 in the embodiment of FIG. 26B has a volume approximately ten times that of the container 108 in the embodiment of FIG. 26A.

The embodiment of FIG. 26C includes two flexible containers 108' and 108" in a parallel relationship, both of which are communicated with the needle hub 140 through frangible seals such as the frangible seal 143 described above, thus permitting the mixing of two liquid drugs during the injection process.

The embodiment of FIG. 26D includes two flexible containers 108' and 108" in series. The first container 108' is separated from the second container 108" by a first frangible seal 143'. The second container 108" is separated from the needle hub 140 by a second frangible seal 143". The first container 108' is filled with a liquid drug component and the second container 108" is filled with a dry drug component. As the roller 210 rolls forward it first pressurizes first container 108' to burst first frangible seal 143' so that the liquid component flows into the second container 108" and begins to mix with the dry drug component. As the roller 210 continues to roll forward the second frangible seal 143" bursts and the mixed liquid and dry drug components are expelled through the needle.

The embodiments of FIGS. 26E-26H show profiled containers 108 which affect the flow rate of delivery of drug from the container 108 as the mechanism rolls a roller across the container to squeeze the medicant out of the container.

In the embodiments of FIGS. 26E-26H the roller 210 is positioned to engage the flexible container 108 and expel the medicant from the container upon relative movement between the roller 210 and container 108 in a displacement direction 211 shown in FIG. 26E. Displacement direction 211 is a longitudinal direction parallel to the axis 128 of cartridge 106. The roller 210 has a rotational axis 213 transverse to that displacement direction 211.

In the embodiment shown in FIG. 26E the flexible container 108 has a width 130 transverse to the displacement direction 211, the width 130 varying along the displacement direction. The roller 210 first engages the container at a first position shown in solid lines and roller 210 moves in the displacement direction toward a second position shown in dotted lines. In the embodiments of FIGS. 26E and 26G, the width 130 of the container 108 at the second engagement position of roller 210 shown in dashed lines is less than the width of the container at the first engagement position, so that the speed of injection of medicant decreases during relative movement of the roller 210 between the first and second engagement positions. This assumes that the roller 210 moves at a constant speed in direction 211. In the embodiments of FIGS. 26E and 26G the width 130 of the container continuously decreases from the first engagement position to the second position.

Conversely, in the embodiment of FIG. 26F, the width of the container 108 at the second engagement position of the roller 210 shown in dashed lines is greater than the width of the container at the first engagement position of the roller shown in solid lines, so that a speed of injection of medicant increases during the relative movement of the roller 210 between the first and second engagement positions.

Finally, as shown in FIG. 26H, the width 130 of the container 108 can vary in multiple aspects. In the embodiment of FIG. 26H, the width 130 first decreases, then increases, which provides an alternating injection speed which first decreases and then increases.

It will be appreciated that the profile of the flexible container can be designed so as to provide any desired changing injection speed profile.

The Multi-Use Dispensing Device

Figure 25:
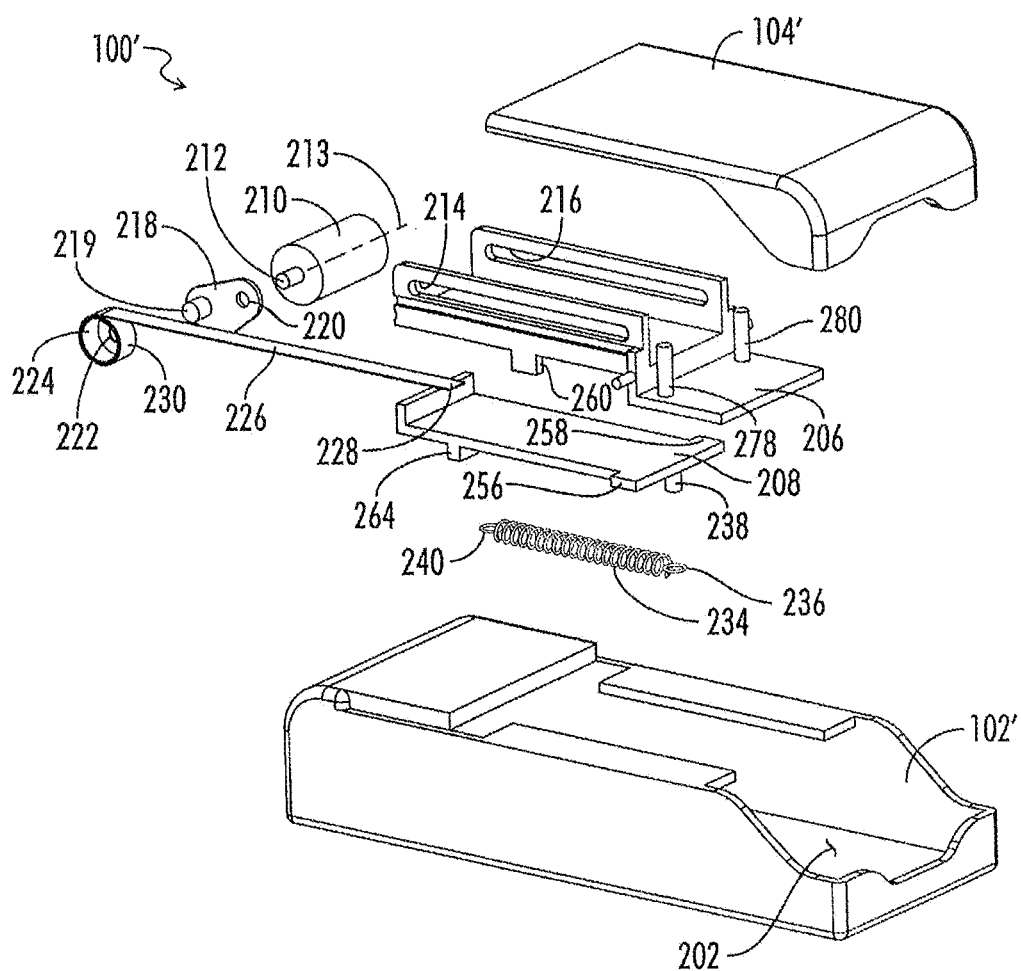
FIG. 25 is an exploded perspective view of an embodiment of an auto-injector apparatus designed for a single use.

The details of construction of those portions of the apparatus 100 other than the cartridge assembly 106 are best shown in FIGS. 10-24. It will be understood that the multi-use apparatus of FIGS. 10-24 and the single use apparatus of FIG. 25 are shown in schematic form in order to illustrate and describe the major internal working components of the device. Further details of the apparatus 100 are explained below with regard to external features of the apparatus 100 which are better shown in the series of FIGS. 2A-2G.

Figure 10:
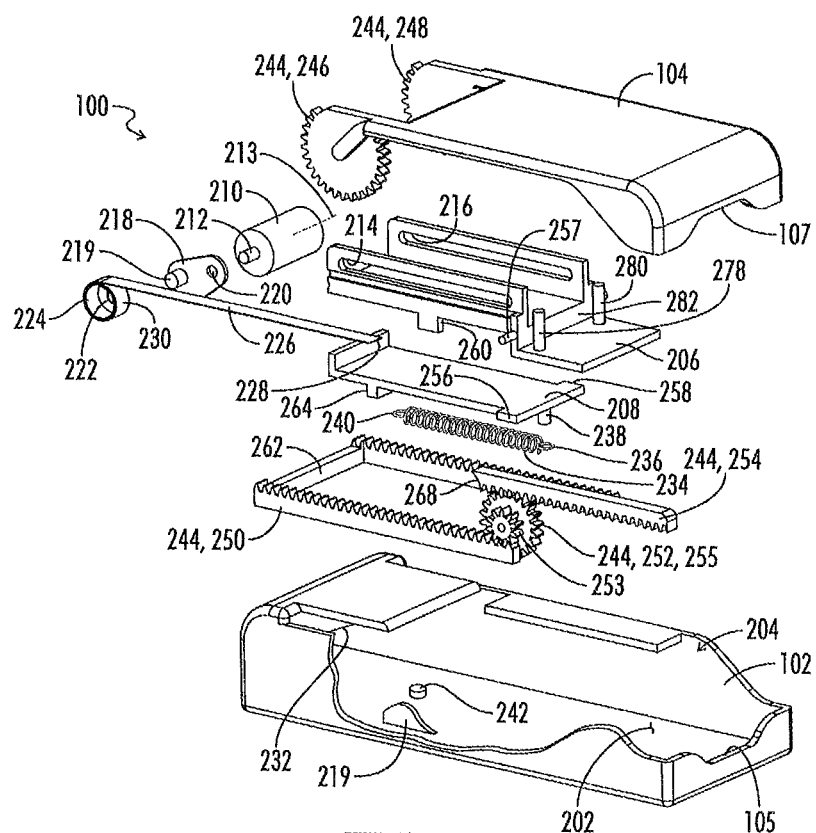
FIG. 10 is an exploded perspective view of an embodiment of an auto-injector apparatus for use with replaceable cartridges.
Figure 13:
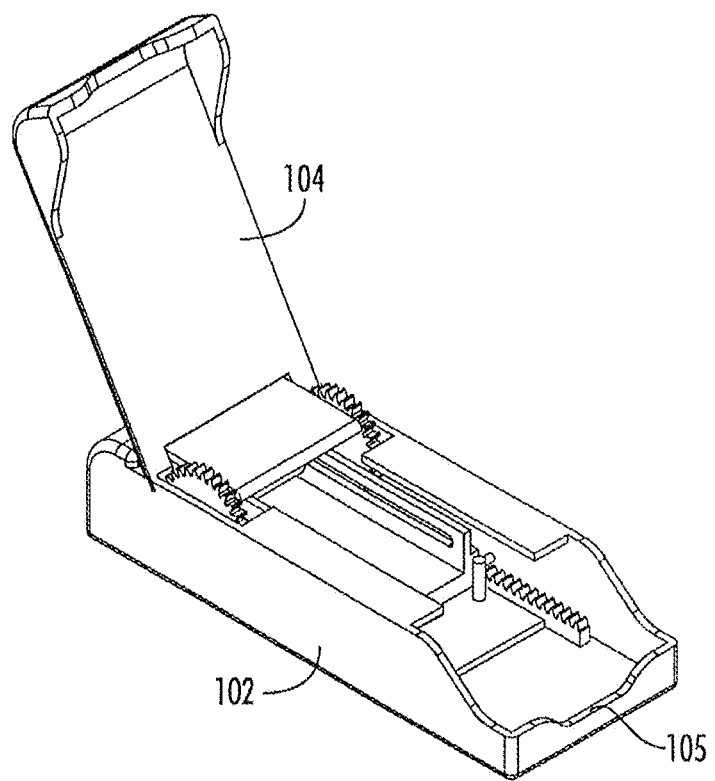

The basic components of the apparatus 100 are most easily understood by viewing the exploded view of FIG. 10. The housing 102, which may be referred to as a main housing body has a housing interior 202 and an opening 204. The lid 104 is pivotally attached to the main housing body 102 and is moveable between a closed position as shown in FIG. 11 closing the opening 204 and an open position as shown in FIG. 13 wherein the housing interior 202 is accessible through the opening 204.

The apparatus 100 includes a container carriage 206 which is reciprocably disposed in the housing body 102. As is illustrated and further described with regard to FIGS. 15 and 16 below, the cartridge assembly 106 including the flexible container 108 will be received in the carriage 206 so that the carriage 206, the container 108 and the needle 144 are moveable together within the housing 102 between a first carriage position illustrated in FIGS. 18, 18A-A and 18B-B and a second carriage position illustrated in FIGS. 20, 20A-A and 20B-B, corresponding to first and second positions of the needle 144, respectively.

A needle return chassis 208 cooperates with the container carriage 206 and is also reciprocably disposed in the housing 102 to aid in withdrawing the needle from its extended position as in FIG. 21 to a retracted safety position as illustrated in FIGS. 23, 24, 24A-A and 24B-B.

A roller 210 includes axles such as 212 extending from each end thereof which extend through roller tracks or slots 214 and 216 defined in the container carriage 206 so as to guide the roller 210 as it rolls in a proximal direction relative to the container carriage 206 to expel medicant from the container 108 as will be further described below.

A roller cam 218 has an opening 220 through which the axle 212 extends. The cam 218 is mounted on the outside of the slot 214. Cam 218 includes a mounting pin 219 which extends through a bore 222 in a spool 224 attached to a main drive spring 226. The main drive spring 226 is a coil spring strip which has a first end 228 fixed to the main housing body 102, and a second end portion 230 which coils around the spool 224 as the main drive spring 226 contracts to its relaxed position. The coil strip spring 226 may provide a substantially constant spring force, and thus may be referred to as a constant force spring. When the main drive spring 226 is uncoiled or extended as shown in FIG. 10 it stores potential energy which is utilized to drive the container carriage 206 proximally to insert the needle 144 into a patient's body and to subsequently drive the roller 210 proximally through the container carriage 206 to roll over the flexible container 108 to expel the medicant therefrom. The main drive spring 226 may be described as being operably associated with the container carriage 206, and thus with the needle 144 attached to the container 108 carried in the container carriage 206, so as to extend the needle 144 from a first needle position as shown for example in FIG. 18A-A wherein the needle 144 is completely received in the housing 102, to a second needle position as shown for example in FIG. 20A-A wherein the needle 144 protrudes from the housing 102.

The main drive spring 226 may also be described as being operably associated with the roller 210 to roll the roller 210 over the flexible container 108 after the needle 144 is extended to its second needle position. As is further explained below with regard to FIGS. 31-34, the roller 210 may be more generally described as a pump 210, and other alternative pump structures may be used in other embodiments.

The roller cam 218 may be further described as a roller interlock between the roller 210 and the container carriage 206 to prevent the roller 210 from rolling over the flexible container 108 until after the main drive spring 226 moves the needle 144 to its second needle position.

As will be further described below with regard to FIG. 14A-A, when the lid 104 is opened the roller cam 218 is forced downwardly against the distal end of the container carriage 206 by a ramp 232 on the outer body 102. Thus the roller cam 218 will prevent the roller 210 from rolling proximally relative to the container carriage 206 until after the container carriage 206 has moved proximally to its second container carriage position as shown for example in FIG. 20A-A.

A retraction spring 234 has a first end 236 connected to a post 238 on the needle return chassis 208 and a second end 240 connected to a post 242 fixed to the bottom floor of the main housing body 102. As is further explained below the retraction spring 234 will, at an appropriate time, pull the needle return chassis 208 and the container carriage 206 and the container 108 and the needle 144 back in a distal direction to withdraw the needle 144 after the medicant has been expelled from the flexible container 108.

The apparatus 100 further includes a cocking linkage 244 connecting the lid 104 to the main drive spring 226 and the retraction spring 234 so that opening of the lid 104 extends the main drive spring 226 and the retraction spring 234. The cocking linkage 244 includes a number of components including gears 246 and 248 integrally formed on the distal end of the lid 104, a main drive rack 250, a drive gear 252, and a spring rack 254. The drive gear 252 includes integrally attached smaller gear 253 and larger gear 255. The drive gear 252 is mounted on an axle 257 extending laterally from the container carriage 206. Thus the drive gear 252 moves laterally with the container carriage 206 within the main housing 102. In the position illustrated in FIG. 10, the small gear 253 is engaged with the gear teeth of the main drive rack 250, and the larger gear 255 is engaged with the gear teeth of the spring rack 254. As is further described below, upon actuation of a trigger 270 the spring rack 254 is shifted laterally relative to drive gear 252 out of engagement with the gear teeth of larger gear 255.

Turning now to FIGS. 11-24 various operating positions of the apparatus 100 are illustrated.

When the apparatus 100 is in the position represented by FIGS. 11, 12, 12A-A and 12B-B, the apparatus 100 is in an unprimed state after a previous injection. For ease of illustration, in views 12A-A and 12B-B no cartridge 106 is shown within the housing, although there would typically be a spent cartridge in place after use of the apparatus 100.

In this position the needle return chassis 208 has moved distally until it abuts a distal end 209 of the housing 102. That movement is accomplished by the needle return spring 234. The container carriage 206 is also in its distalmost position to which it was carried by engagement of lateral tabs such as 256 and 258 (see FIG. 10) defined on needle return chassis 208 with vertical tabs such as 260 extending downward from container carriage 206. In the position of container carriage 206 shown in FIG. 12A-A the main drive spring 234, which for ease of illustration is not shown in FIG. 12A-A or 12B-B, is in a partially extended position to which it has been carried by contraction of the return spring 234. As shown in FIG. 12B-B the roller 210 is in a proximalmost position relative to container carriage 206 to which position the roller 210 rolled during the prior actuation of the apparatus 100.

Moving now from the position of FIGS. 11 and 12 to the position of FIGS. 13 and 14, when the user opens the apparatus 100 by lifting the lid 104 from the body 102 the main drive rack 250 is driven forward or proximally thus forcing the needle return chassis 208 forward due to engagement of a cross bar 262 of main drive rack 250 with a downward extending foot 264 of needle return chassis 208. This extends the needle retraction spring 234. A first trigger 266 shown schematically in FIG. 14A-A will engage the needle return chassis 208 to prevent the chassis 208 from moving rearwardly or distally after the retraction spring 234 has been stretched to full extension as shown in FIG. 14A-A.

Furthermore, in the position of FIG. 14A-A the roller 210 has been forced to its distalmost position wherein the roller cam 218 has engaged the ramp 232 and has moved downward to hold the roller 210 in its distalmost position relative to the container carriage 206. When the roller 210 is forced distally this also serves to extend the main drive spring 226. These movements have been accomplished by the cocking linkage 244 upon opening of the lid 104 in the following manner. As the lid 104 pivots upwardly away from the main housing body 102 the gears 246 and 248 which are meshed with the teeth of the main drive rack 250 force the main drive rack 250 to move proximally within the housing 102. As the main drive rack 250 moves in a proximal direction, it rotates the drive gear 252 which is rotatably mounted on axle 257 (see FIG. 10) of container carriage 206. As the drive gear 252 rotates, its larger gear member is in engagement with the spring rack 254 which drives the spring rack 254 in the opposite direction from the main drive rack 250. Thus the spring rack 254 moves in a distal direction and its distal end 268 is engaged with the coil portion 230 of main drive spring 226 and moves the coil portion 230 distally thus unwinding and stretching or extending the main drive spring 226.

A second trigger 270 schematically illustrated in FIG. 14B-B prevents the container carriage 206 from moving forward or proximally.

Figure 15:
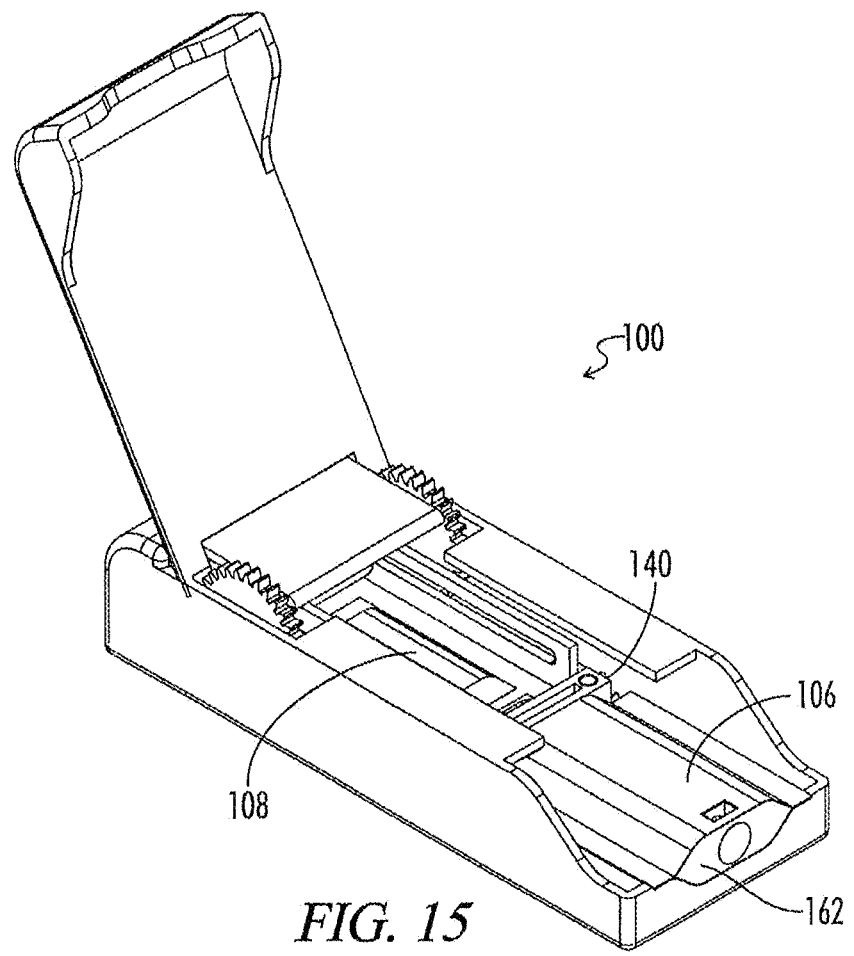

With the apparatus 100 in the open position as shown in FIG. 13, a cartridge assembly 106 can be placed therein as illustrated in FIG. 15.

Then as shown in FIGS. 17 and 18, the lid 104 is closed and the apparatus 100 is now primed and ready for use. As shown in FIGS. 18A-A and 18B-B, closing the lid 104 returns the main drive rack 250 to its distalmost position leaving the needle return chassis 208 in its cocked or primed position. As previously noted the needle return chassis is held in position by first trigger 266.

Next, a proximal end 272 of the apparatus 100 is held against the patient's body and second trigger 270 is fired manually to shift the spring rack 254 sideways thus demeshing the spring rack 254 from the drive gear 252. This releases the container carriage 206 so that the container carriage 206 is driven forward or proximally by the main drive spring 226. The container carriage 206 carries with it the container 108 and the needle hub 140 and needle 144. The needle 144 is driven forward or proximally to the position shown in FIGS. 19 and 20. During that movement, the needle protection frame 154 of cartridge assembly 106 has remained fixed relative to the housing 102 while the needle hub 140 slides proximally over the arms 158 and 160 to a position like that shown in FIG. 8B.

Thus as the apparatus 100 moves from its position as illustrated by FIGS. 17 and 18 to its position as illustrated by FIGS. 19 and 20, the needle hub 140 and needle protection frame 154 move relatively between their positions as shown in FIG. 8A to their position as shown in FIG. 8B.

It is noted that in FIG. 20, the roller 210 still has not moved forward within the container carriage 206, because the roller cam 218 has held the roller 210 in place.

As the container carriage 206 moves forward the roller cam 218 reaches the end stop on a ramp 219' (see FIG. 10) on the outer body 102 which forces the roller cam 218 upward thus releasing the roller 210 and allowing the roller 210 to move proximally along the tracks 214 and 216 thus rolling over the flexible container 108 to expel the medicant therefrom. The roller 210 moves from its position as shown in FIG. 20B-B to its position as shown in FIG. 22B-B. The roller 210 is driven forward or proximally relative to the container carriage 206 by the further contraction of the main drive spring 226. When the roller 210 reaches its forwardmost position as shown in FIG. 22B it trips trigger 266 thus releasing the needle return chassis 208 which is then drawn backward or distally due to contraction of the retraction spring 234 thus pulling the needle return chassis 208 and the container carriage 206 along with the cartridge assembly 106 and the needle 144 back to their starting positions as shown in FIGS. 23 and 24 wherein the needle 144 is once again withdrawn to a safety position within the housing 202.

During that return motion, the main drive spring 226 is partially extended when the container carriage 206 pulls back the roller 210 from the position shown in FIG. 22B-B to the position shown in FIG. 24B-B. The apparatus 100 in FIGS. 23 and 24 is now back in the same position at which it began in FIGS. 11 and 12.

The first trigger 266 may be described as an interlock 266 operably associated with the needle return chassis 208 and the container carriage 206. The interlock 266 releases the needle return chassis 208 after the roller 210 expels the medicant from the container 108 so that the retraction spring 234 can withdraw the needle return chassis 208, the container carriage 206, the container 108 and the needle 144 to a safety position wherein the needle 144 is fully received back in the housing.

Thus, the apparatus 100 is in condition to again be opened and have the cartridge assembly 106 replaced. Thus the apparatus 100 is a multi-use apparatus which can be used any number of times by replacing the cartridge 106 after use.

When the cartridge 106 is placed in the container carriage 206 two openings 274 and 276 (see FIG. 5) in the needle hub 140 receive two posts 278 and 280 (see FIG. 10) extending upward from the container carriage 206. A wall 282 of container carriage 206 engages a wall 284 (see FIG. 5) of needle hub 140. When the cartridge 106 is in place in the apparatus 100 the front bar 162 of cartridge 106 is closely received in recesses 105 and 107 of housing body 102 and lid 104, respectively, as shown in FIGS. 15 and 17.

Then when the container carriage 206 moves forward in later stages of operation it immediately moves the needle hub 140 forward while the needle protection frame 154 remains fixed in place relative to the housing 102.

Interlock Requirements

The following Table II describes the required interlocks through one complete injection cycle for apparatus 100. In Table II the flexible container 108 is referred to as a sachet.

TABLE II

| Device State | Sachet | Failure Mode | Interlock Required | Skin Contact | Trigger | Lid closed | No Sachet | Full sachet in place | Device Fires |
|---|---|---|---|---|---|---|---|---|---|
| Device closed - Drug delivered | None | None | None | 1 | 0 | 1 | 0 | 0 | No |
| Device open - Primed | None | Device Fires, lid snaps shut. High impact on end stops | Device cannot fire with lid | 1 | 1 | 0 | 0 | 0 | No |

TABLE II-continued

| Device State | Sachet | Failure Mode | Interlock Required | Skin Contact | Trigger | Lid closed | No Sachet | Full sachet in place | Device Fires |
|---|---|---|---|---|---|---|---|---|---|
| | | without sachet to dampen forces. | open | | | | | | |
| Device primed - Closed | None | Device mechanism damaged hitting end stops hard if fired. Mechanism abuse possible (biro type playing) | Device cannot fire without a sachet in position | 1 | 1 | 1 | 0 | 0 | No |
| Device open - Primed | Full | Device Fires, lid snaps shut, Drug delivered without body contact | Device cannot fire with lid open | 1 | 1 | 0 | 1 | 1 | No |
| Device primed - Closed | Full | Device fires when not in contact with skin, dose lost | Device will only fire with skin contact | 1 | 1 | 1 | 1 | 1 | Yes |
| Device closed - Drug delivered | Used | None | None | 1 | 0 | 1 | 1 | 0 | No |
| Device open - Primed | Used | Device mechanism damaged hitting end stops hard if fired. Used needle fires again | Device cannot fire with lid open | 1 | 1 | 0 | 1 | 0 | No |
| Device primed - Closed | Used | Used needle fires a second time | Sachet locked after use | 1 | 1 | 1 | 1 | 0 | No |

The device trigger 270 must only become unlocked when skin contact is made with the needle end of the device 100.

The 'no sachet' interlock and 'used sachet' interlock could become one feature if there was a permanently displaceable component on the container carriage 208 that interacted with the 'no sachet' interlock.

The 'lid closed' interlock must be well recessed to prevent activation by any means other than the lid 104 being closed in place. This may include multiple contact points.

Fixed Roller Embodiments of FIGS. 27-30

FIG. 27

In the embodiments of FIGS. 1-24 described above, during the relative movement between the roller and the flexible container wherein the medicant is expelled from the flexible container, the flexible container has been held in a fixed position relative to the housing and the roller has moved longitudinally relative to the housing to roll over the flexible container to expel the medicant. It is also possible to achieve the same relative motion between the roller and the flexible container by holding the roller in a fixed position relative to the housing while moving the flexible container in a longitudinal direction relative to the housing. Several such arrangements are schematically illustrated in FIGS. 27-30.

Figure 27:
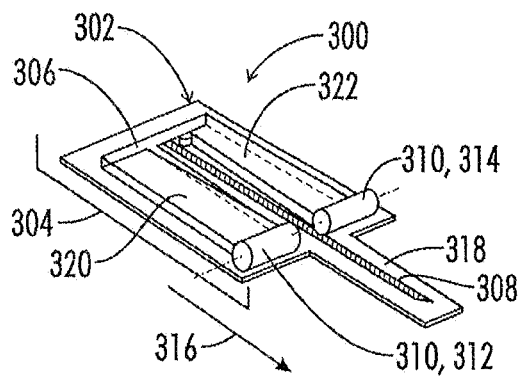
FIG. 27 is a schematic perspective view of an embodiment of an injection apparatus having a longitudinally fixed roller.

FIG. 27 schematically shows an injection apparatus 300 including a cartridge 302 carried in a container carriage 304. The container carriage 304 functions in a manner similar to the container carriage 206 described above and is powered by a main drive spring (not shown) which may be a coil strip main drive spring similar to drive spring 226 described above. The carriage 304 and the drive spring are received in a housing (not shown) similar to housing 102 described above.

The cartridge 302 includes a needle hub 306 having a needle 308 extending proximally therefrom. A roller 310 having first and second coaxial spaced roller portions 312 and 314 is longitudinally fixed relative to the housing so that the roller 310 rotates relative to the housing but does not move longitudinally relative to the housing. The needle 308 extends between the roller portions 312 and 314. The roller portions 312 and 314 engage first and second flexible containers 320 and 322 which are communicated at their distal ends with needle hub 306 and thus with needle 308.

As the container carriage 304 begins moving in the direction 316 relative to the housing and relative to the longitudinally fixed rollers 310, the needle 308 will pierce a flexible needle protective sleeve 318 and will be inserted into a patient's body. Further movement of the container carriage 304 moves the first and second flexible container compartments 320 and 322 past the fixed rollers 312 and 314 so that the rollers squeeze the medicant contained in the flexible containers 320 and 322 out through the needle hub 306 and through the needle 308 into the patient's body.

With the embodiment of FIG. 27, as the container carriage 304 moves forward the needle 308 will continue to be inserted deeper into the patient's body while the medicant is simultaneously being expelled through the needle 308 into the patient's body. Thus some portion of the needle insertion and the drug injection can occur simultaneously.

In all applicable respects other than the geometry of the arrangement, the details of construction of the flexible containers 320 and 322, the needle hub 306 and other components of the apparatus 300 will be similar to those of the apparatus 100 described in detail above.

FIG. 28

Figure 28:
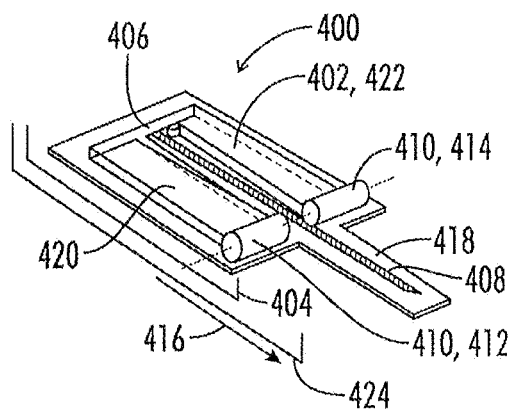
FIG. 28 is a schematic perspective view of another embodiment of an injection apparatus having a longitudinally fixed roller.

FIG. 28 schematically illustrates an embodiment somewhat similar to that of FIG. 27, except in the embodiment of FIG. 28, a secondary carriage is provided to first partially insert the needle into the patient's body.

Thus in FIG. 28 an apparatus 400 is shown including a cartridge 402 carried in a container carriage 404 which is in turn carried in a secondary carriage 424. The apparatus 400 includes needle hub 406, needle 408, roller 410 with roller portions 412 and 414, sheath 418 and flexible containers 420 and 422 all similar to the analogous components described above with regard to FIG. 27. The roller portions 412 and 414 are longitudinally fixed to the secondary carriage 424.

The secondary carriage 424 carries the container carriage 404 and accompanying components to initially insert the needle 408 into the patient's body. Then further motion of the container carriage 404 relative to the secondary carriage 424 moves first and second flexible container compartments 420 and 422 past first and second roller portions 412 and 414 of roller 410 in the direction 416 to expel the medicant from the container portions 420 and 422 and into the patient.

The motion of container carriage 404 relative to secondary carriage 424, and the motion of secondary carriage 424 relative to the housing (not shown) may be driven by any suitable spring or other power source, such as coil strip springs like 226 or helical springs like 234.

FIG. 29

Figure 29:
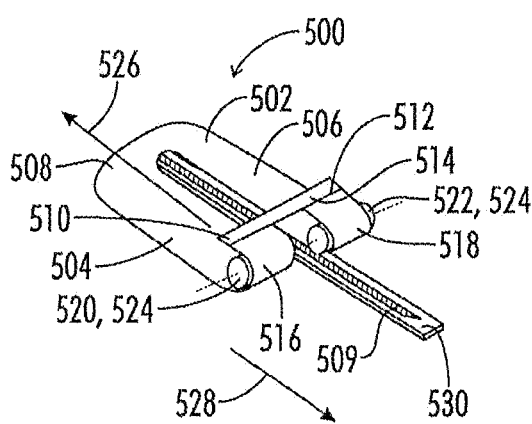
FIG. 29 is a schematic perspective view of another embodiment of an injection apparatus having a longitudinally fixed roller.

FIG. 29 schematically illustrates another embodiment of the fixed roller apparatus which is generally designated by the numeral 500.

The apparatus 500, similar to the apparatus 300 of FIG. 27, includes a U-shape or dual chamber flexible container 502 having first and second container portions 504 and 506. A bottom portion 508 of the U-shape flexible container 502 may include a needle hub similar to the needle hub 306 and similar to the needle hub 140 described above.

A needle 509 extends proximally from the needle hub 508. Proximal ends 510 and 512 of the flexible container portions 504 and 506 are attached to a pull bar 514. Intermediate portions 516 and 518 of the first and second container portions 504 and 506 are wrapped around first and second roller portions 520 and 522 of roller 524. The roller 524 is fixedly attached to the apparatus housing (not shown) so as to rotate relative to the housing without moving longitudinally relative to the housing.

A main drive spring (not shown) attached to the pull bar 514 pulls the pull bar 514 in a distal direction as indicated by arrow 526. This causes the portions of the flexible containers 504 and 506 located above the roller 524 to be pulled distally while the portions of the flexible containers 504 and 506 located below the roller 524 move proximally in the direction indicated by arrow 528.

As those lower portions of the flexible container move proximally, they pull forward the needle hub 508 and the attached needle 509 moving them proximally so as to insert the needle 509 in the patient and to expel medicant from the container portions 504 and 506 through the needle 509 into the patient. The container portions 504 and 506 may initially be only partially filled so that the initial forward motion of needle 509 to insert the needle into the patient's body may occur before the drug begins to be expelled through the needle.

With the embodiment of FIG. 29 the initial proximal movement of the needle 509 serves to collapse a needle protection sheath 530 and insert the needle 509 into the patient, and continued proximal movement of the needle 509 will further insert the needle 509 into the patient while medicant is simultaneously expelled from the flexible container portions 504 and 506 through the needle 509 into the patient.

FIG. 30

Figure 30:
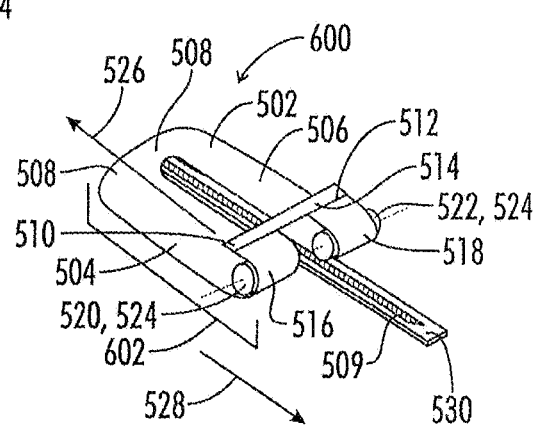
FIG. 30 is a schematic perspective view of another embodiment of an injection apparatus having a longitudinally fixed roller.

FIG. 30 schematically illustrates a further embodiment identified by the numeral 600 which is similar to the embodiment of FIG. 29 except that it adds a secondary carriage 602. Other components are numbered the same as in FIG. 29.

The secondary carriage 602 provides an initial proximal movement in direction 528 of the entire flexible container 502 and associated structures of FIG. 29, to an initial position which will insert the needle 509 into the patient. Then a main drive spring (not shown) initiates the motion of the pull bar 514 in the direction 526 relative to the secondary carriage 602 and the main housing to further inject the needle 509 and expel the medicant from the flexible container 502.

In general, with regard to all of the embodiments described above, the roller can be said to engage its associated flexible container and expel the medicant from the container through the needle upon relative movement between the roller and the container. In each case the roller has a rotational axis and the relative movement between the roller and the container is a relative longitudinal movement in a longitudinal direction transverse to the rotational axis.

In some embodiments such as those of FIGS. 10-25, the flexible container is longitudinally fixed relative to the housing during the injection process, and the roller moves longitudinally relative to the container and the housing. In other embodiments such as FIGS. 27-30, the roller is longitudinally fixed relative to the housing during the injection process, and the container moves longitudinally relative to the roller and the housing.

Single Use Embodiment of FIG. 25

FIG. 25 is a schematic perspective exploded view of a single use embodiment of the auto-injector apparatus. FIG. 25 is similar in many aspects to FIG. 10, and those components of FIG. 25 identical to the components of FIG. 10 are identified with the same numerals as used in FIG. 10, and those components which have been modified are indicated with a prime suffix. Thus the apparatus of FIG. 25 is referred to as the apparatus 100'. The housing includes a main housing body 102' and a lid 104', however the lid is not designed for repeated opening and closing. Instead, the lid 104' is designed to be permanently attached to the main housing body 102' so that the housing 102', 104' comprises a closed single use housing having an interior 202 which is inaccessible by a user without damage to the housing.

The single use apparatus 100' may utilize the same container carriage 206, roller 210, roller cam 218, main drive spring 226, return chassis 208, and retraction spring 234 as were described above with regard to the multi-use apparatus 100.

The primary deletions from the apparatus 100 of FIG. 10 include the cocking linkage 244 and its gears 246 and 248, the main drive rack 250, the drive gear 252, and the spring rack 254, all of which have been eliminated because there is no need for opening of the housing or reloading of the housing with a cartridge.

Although not shown in FIG. 25, the single use apparatus 100' will use the same cartridge assembly 106 as described above, which will be carried in the container carriage 206 in the same manner as described above with regard to the apparatus 100. The difference is that a single cartridge 102 will be placed within the apparatus 100' prior to sealing the lid 104' on the main housing body 102', and there is no replacement of that cartridge after use. Thus when the apparatus 100 is assembled, a cartridge 106 is placed within the cartridge carrier 206. The roller 210, roller cam 218, main drive spring 226, container carriage 206, return chassis 208 and retraction spring 234 are all placed in positions analogous to those shown in FIGS. 17, 18, 18A-A and 18B-B. The triggers 266 and 270 as shown in FIG. 18A-A are in place.

External Packaging For Single Use Embodiment

Figure 41:
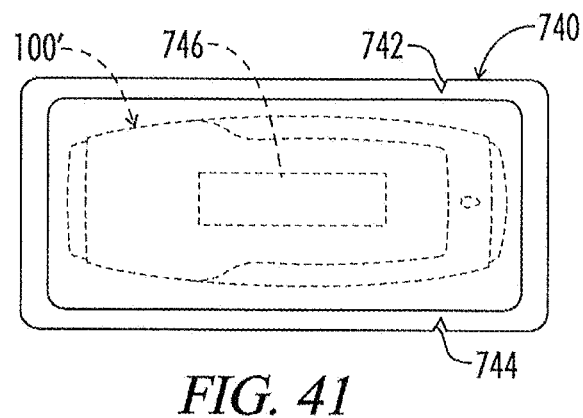
FIG. 41 is a plan view of a single use injector device contained in secondary packaging.
Figure 42:
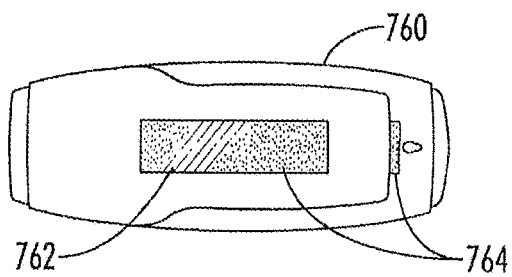
FIG. 42 is a plan view of a single use device having a transparent window covered by a pull strip.
Figure 43:
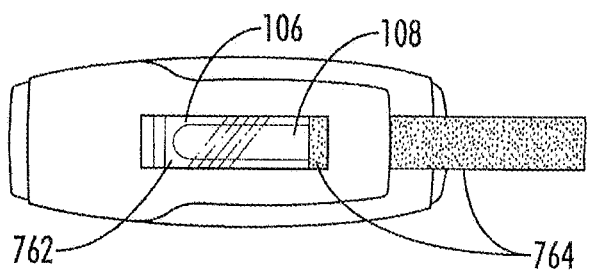
FIG. 43 shows the device of FIG. 42 after the pull strip has been pulled to expose the cartridge through the transparent window.

FIGS. 41 and 42-43 show two different types of external packaging that can be used with the single use injector device 100'.

In FIG. 41 the device 100' is contained in an opaque, preferably metal foil, outer package 740 which is constructed like the package 700 described above with regard to FIG. 35. Package 740 has notches 742 and 744 which allow the user to tear the package open to access the single use device 100'. The device 100' has a transparent window 746 formed in the front thereof so that the flexible container 108 of the cartridge 106 contained therein may be viewed to confirm that the container 108 is filled with medicant prior to use of the device 100'.

FIGS. 42 and 43 show a single use device 760 similar to the device 100' of FIG. 25, but with a transparent widow 762 formed in the front thereof. The window 762 is initially blocked in FIG. 42 by an opaque pull strip 764. Prior to use of the apparatus 760, the strip 764 is pulled to a second position as shown in FIG. 43, thus exposing the cartridge 106 to view through the transparent window 762. This allows the transparent flexible container 108 of the cartridge 106 to be viewed through the window 762 to confirm that the container 108 is full of medicant prior to use of the device 760, and to confirm that the medicant is clear and free of particulates. A second transparent window and pull strip is preferably provided on the other side of the device 760 to allow a see through inspection of the container 108. The pull strips preferably are constructed as integral portions of a secondary package around the flexible container 108, so that portions of the package are peeled back to expose the container 108 when the pull strips are pulled. The secondary container including the pull strips should block exposure of the container 108 to light passing through the window 762 prior to pulling the pull strips.

Methods of Use

The methods of use of the apparatus will now be described with regard to FIGS. 9-24 and the schematic views of FIGS. 2A-2G.

One example of a method of auto-injecting a liquid medicant into a patient may include:

(a) Placing a proximal end 272 of an auto-injector apparatus 100 or 100' against a patient's body 101—the patient's body 101 is only schematically illustrated and may for example be an arm or thigh of the patient such as typically used as an injection site;

(b) Releasing a main drive spring 226 such as for example by manually releasing second trigger 270 by depressing the same as indicated by arrow 103 in FIG. 2E;

(c) Driving the needle 144 proximally within the apparatus 100 or 100' with the main drive spring 226 so that the needle 144 extends out of the proximal end 272 of the apparatus 100 or 100' thereby inserting the needle 144 in the patient's body 101; and (d) Creating relative motion between roller 210 and flexible container 108 by rolling the roller 210 over the flexible medicant container 108 within the apparatus 100 or 100' with the main drive spring 226 after or while the needle 144 is being inserted in the patient's body 101 and thereby forcing the medicant out of the medicant container 108 through the needle 144 into the patient's body 101. During the relative motion between the roller and the flexible container to force the medicant out of the container, a frangible seal within the flexible medicant container is broken so that the medicant can flow from the container to the needle.

After injecting the medicant into the patient's body, the needle return chassis 208 is released to retract the needle 144 back into the apparatus 100 or 100' with the retraction spring 234 as shown for example in FIG. 2G and in FIGS. 23, 24, 24A-A and 24B-B.

Those steps just described are applicable to both the multi-use apparatus 100 of FIGS. 10-24 and the single use apparatus 100' of FIG. 25.

For the multi-use apparatus 100 of FIGS. 10-24, the apparatus can further be reloaded by opening the lid 104 of the apparatus 100 to provide access to the interior 202. That opening action extends the main drive spring 236 and the retraction spring 234 so that the springs 236 and 234 are in position to repeat the insertion of the needle and injection of the medicant into the patient. After opening the lid, the spent medicant container 106 including its needle 144 is removed from the apparatus 100 and a new medicant container and needle assembly 106 are placed in the apparatus 100.

The overall method of operation of the multi-use apparatus 100 of FIGS. 10-24 is schematically illustrated in the seven sequential positions set forth in FIGS. 2A-2G. It is noted that the seven steps represented by FIGS. 2A-2G correspond to the seven positions of the apparatus 100 illustrated in FIGS. 11, 13, 15, 17, 19, 21 and 23, respectively.

Thus, in FIG. 2A, FIG. 11, FIG. 12, FIG. 12A-A and FIG. 12B-B, the apparatus 100 begins in an unprimed state after the previous injection.

In FIG. 2B, FIG. 13, FIG. 14, FIG. 14A-A and FIG. 14B-B the lid 104 of the apparatus 100 has been opened. This has reset the main drive spring 226 and the retraction spring 234, and has moved roller 210, container carriage 206 and needle return chassis 208 to the positions illustrated in FIGS. 14A-A and 14B-B.

In FIG. 2C, FIG. 15, FIG. 16, FIG. 16A-A and FIG. 16B-B a new cartridge assembly 106 has been inserted into the apparatus 100.

In FIG. 2D, FIG. 17, FIG. 18, FIG. 18A-A and FIG. 18B-B the lid 104 has been closed and the apparatus 100 is primed and ready for use.

In FIG. 2E, FIG. 19, FIG. 20, FIG. 20A-A and FIG. 20B-B the distal end 272 of the apparatus 100 is held against the patient's body 101 and the trigger 270 is fired manually by the user depressing the same with a thumb as indicated by arrow 103. The trigger 270 shifts the spring rack 254 sideways thus demeshing it from the drive gear 252 which releases the container carriage 206 which is then driven forward by the main drive spring 226 thus driving the needle 144 into the patient's body 101.

It is noted that in FIG. 2E the needle 144 is not shown, whereas the needle 144 is shown protruding from the housing 102 in FIGS. 19 and 20. It will be understood that as a result of actuating the trigger 270 as indicated in FIG. 2E the needle 144 will move forward and will protrude from the apparatus 100 into the patient's body 101 as shown for example in FIG. 2F.

FIG. 2F, FIG. 21, FIG. 22, FIG. 22A-A and FIG. 22B-B illustrate the position of the various components of the apparatus 100 after the main drive spring 226 has driven the roller 210 forward to expel the liquid medicant from the flexible container. When the roller reaches the end of its travel it trips trigger 266.

FIG. 2G, FIG. 23, FIG. 24, FIG. 24A-A and FIG. 24B-B illustrate the position of the components after trigger 266 has released the needle return chassis 208 so that the retraction spring 234 draws the needle return chassis 208, the container carriage 206 and the cartridge assembly 106 back within the housing thus withdrawing the needle 144 from the patient.

In the arrangement just described with reference to FIGS. 2A-2G the proximal end 272 was first pressed against the patient's body to arm the device, and then trigger 270 was pressed to fire the device. Alternatively the various interlocks between the operating components can be arranged so that the trigger 270 must first be pressed to arm the device, and then when distal end 272 is pressed against the patient's body the device will automatically fire.

The Alternative Pump Embodiments of FIGS. 31-34

FIGS. 31A-31B

As previously noted, the roller 210 may be generally described as a pump 210 disposed in the housing and positioned to engage the flexible container 108 and expel the medicant from the container 108 through the needle 144. FIGS. 31-34 schematically illustrate alternative pump arrangements which could be substituted for the roller pump 210.

Figure 31A:
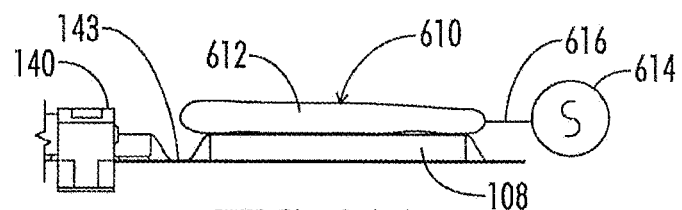
FIGS. 31A and 31B schematically show two positions of an alternative pump apparatus including an inflatable balloon pump.
Figure 31B:
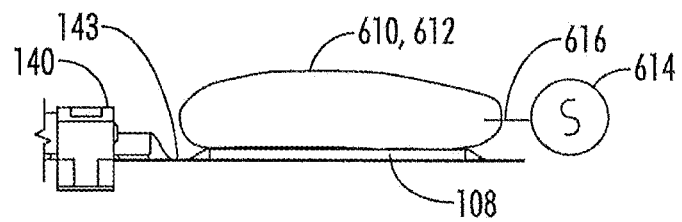

In FIGS. 31A and 31B a pump 610 includes an inflatable balloon or bladder 612 powered by compressed gas or expanding chemical reaction producing reaction gases from gas source 614 via conduit 616.

In FIG. 31A the balloon pump 610, 612 is schematically shown in an uninflated position. In FIG. 31B the pump 610, 612 is schematically shown in an inflated position. As the balloon 612 inflates within the housing, it acts against the flexible container 108 thus compressing the flexible container 108 to a compressed condition as shown in FIG. 31B which expels the medicant from the container 108 through the frangible seal 143 to the needle hub 140. The expanding balloon 612 applies pressure to the flexible container 108 thus squeezing the flexible container 108 from its original condition shown in FIG. 31A to its compressed position shown in FIG. 31B.

FIGS. 32A-32B

Figure 32A:
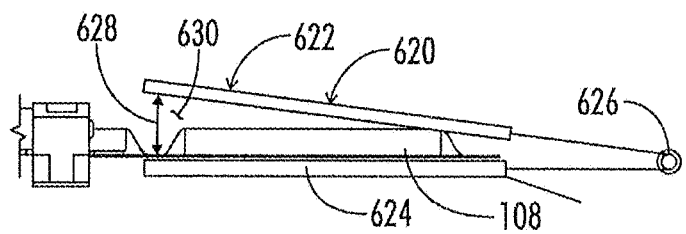
FIGS. 32A and 32B schematically show two positions of an alternative pump apparatus including a pair of magnets on opposite sides of the flexible container.
Figure 32B:
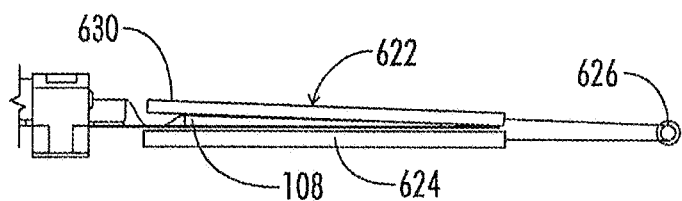

Referring now to FIGS. 32A-32B, a magnetic pump 620 includes a pair of magnets 622 and 624. The magnets at one end are pivotally connected at 626. At the other end a mechanical blocking device schematically indicated at 628 holds the magnets apart so as to define a gap 630 therebetween within which the flexible container 108 is located. Upon removing the mechanical blocker 628, the magnet 622 moves toward the magnet 624 thus closing the gap 630 and applying pressure to the flexible container 108 to collapse the flexible container 108 to a position such as schematically illustrated in FIG. 32B, thus expelling the medicant from the flexible container 108. The magnetic pump 620 can be described as comprising a pair of magnets 622 and 624 on opposite sides of the flexible container 108.

FIGS. 33A-33B

Figure 33A:
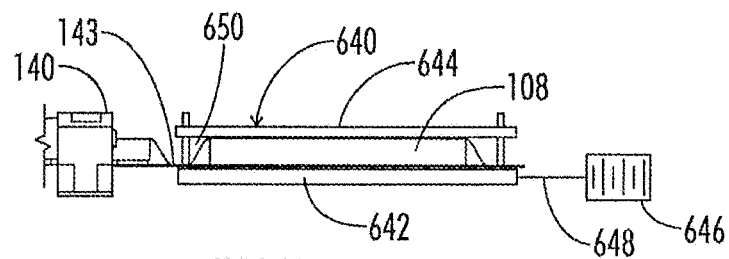
FIGS. 33A and 33B schematically show two positions of an alternative pump apparatus including an electromagnet and a magnetically attracted mass.
Figure 33B:
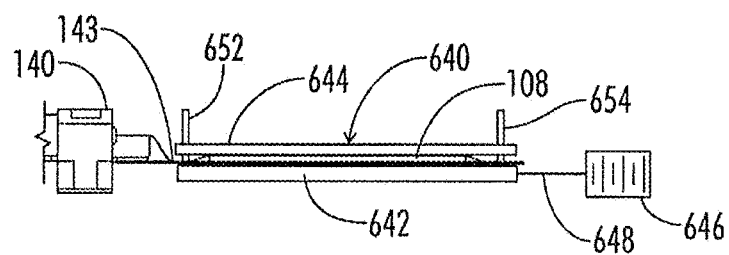

FIGS. 33A-33B schematically illustrate an electromagnetic pump 640 which includes an electromagnet 642 and a magnetically attractive mass 644 on opposite sides of the flexible container 108. The electromagnet 642 may be an electric coil type magnet which receives electrical power from battery 646 via wires 648. The magnetically attractive mass 644 may be a steel plate. In the unactuated position of FIG. 33A a gap 650 is defined between electromagnet 642 and steel plate 644, and the flexible container 108 is located in the gap 650.

When current from battery 646 is applied to the coil of electromagnet 642 the steel plate 644 is drawn toward electromagnet 642 thus closing the gap 650 and compressing the flexible container 108 to a condition like that schematically illustrated in FIG. 33B, thus squeezing the medicant out of the flexible container 108 through the frangible seal 143 to the needle hub 140. The steel plate 644 may ride on guideposts 652 and 654 extending upwardly from the electromagnet 642.

FIGS. 34A-34B

Figure 34A:
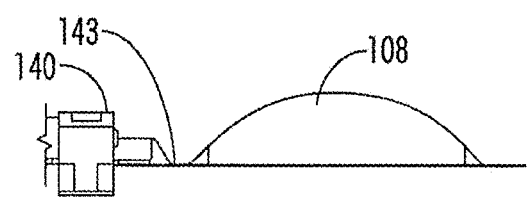
FIGS. 34A and 34B schematically show two positions of an alternative pump apparatus including a source of fluid pressure communicated with the interior of the flexible container.
Figure 34B:
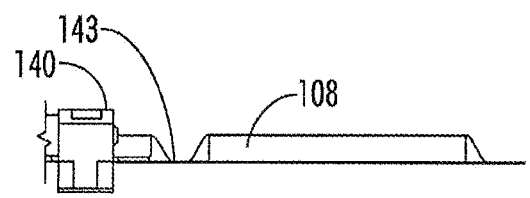

FIGS. 34A and 34B schematically illustrate an alternative pump apparatus 660 wherein the pump comprises construction of the flexible container 108 from a resilient material so the container can be pressurized to an expanded position as shown in FIG. 34A. When it is desired to expel the medicant from the flexible container 108, the frangible seal 143 is breached by any suitable means, thus allowing the stretched walls of container 108 to retract to the position of FIG. 34B, thus forcing the medicant out of container 108 and past breached seal 143 to needle hub 140.

Thus it is seen that the apparatus and methods of the present invention readily achieve the ends and advantages mentioned as well as those inherent therein. While certain preferred embodiments of the invention have been illustrated and described for purposes of the present disclosure, numerous changes in the arrangement and construction of parts and steps may be made by those skilled in the art, which changes are encompassed within the scope and spirit of the present invention as defined by the appended claims.

What is claimed is:

1. An auto-injector apparatus, comprising:
    a flexible container containing a liquid medicament;
    a needle communicated with the container;
    a housing, the container being received in the housing;
    a pump disposed in the housing and positioned to engage the flexible container and expel the medicament from the container through the needle upon relative movement between the pump and the container, wherein the pump contains a roller;
    a main drive spring operably associated with the needle to extend the needle from a first needle position wherein the needle is completely received in the housing to a second needle position wherein the needle protrudes from the housing; and
    a retraction spring operably associated with the needle to retract the needle back into the housing after the medicament is expelled from the container.

2. The apparatus of claim 1, wherein: the main drive spring is operably associated with the pump to create the relative movement between the pump and the flexible container.

3. The apparatus of claim 1, wherein: the housing further comprises a housing body having a housing interior and an opening, and a housing lid movably attached to the housing body, the lid being movable between a closed position closing the opening and an open position wherein the housing interior is accessible through the opening.

4. The apparatus of claim 3, further comprising: a cocking linkage connecting the lid to the main drive spring and the retraction spring so that opening of the lid extends the main drive spring and the retraction spring.

5. The apparatus of claim 1, further comprising: a container carriage reciprocally disposed in the housing, the container being received in the carriage so that the carriage, the container and the needle are movable together within the housing between first and second carriage positions corresponding to the first and second needle positions.

6. The apparatus of claim 5, further comprising: a needle return chassis containing the needle; wherein the retraction spring of claim 1 is connected between the housing and the needle return chassis containing the needle; an interlock operably associated with the needle return chassis and the container carriage, the interlock releasing the needle return chassis after the pump expels the medicament from the container so that the retraction spring can withdraw the needle containing return chassis, the container carriage, the container and the needle to a safety position wherein the needle is fully received back in the housing.

7. The apparatus of claim 5, wherein: the container carriage includes a roller track; and the roller is received in the roller track so that the roller is guided by the roller track as the roller rolls over the flexible container.

8. The apparatus of claim 7, further comprising: a roller interlock between the roller and the container carriage to prevent the roller from rolling over the flexible container until after the main drive spring moves the needle to its second needle position.

9. The apparatus of claim 1, wherein: the flexible container and the needle are connected together as part of a replaceable cartridge assembly replaceably received in the housing; and the pump and the main drive spring are connected to the housing for multiple use with sequential replaceable cartridge assemblies.

10. The apparatus of claim 1, further comprising: a needle hub connected to the flexible container, the needle being attached to the needle hub and including a needle proximal end extending proximally from the needle hub; and a needle protection frame slidably connected to the needle hub, the needle hub being slidable relative to the frame from a first hub position wherein the frame extends proximally beyond the needle proximal end, to a second hub position wherein the needle proximal end extends proximally beyond the frame.

11. The apparatus of claim 10, further comprising: a collapsible needle sheath supported by the frame and covering the needle to aid in maintaining sterility of the needle when the needle hub is in its first hub position relative to the frame.

12. The apparatus of claim 1, wherein: the main drive spring comprises a coiled spring strip.

13. The apparatus of claim 1, wherein: the housing comprises a closed single use housing having an interior inaccessible by a user without damage to the housing.

14. The apparatus of claim 13, further comprising: the housing having a transparent window therein through which the flexible container is visible; and an opaque secondary container in which the housing is sealed.

15. The apparatus of claim 13, further comprising: the housing having a transparent window therein through which the flexible container can be viewed; and a pull strip movable between a first position blocking the transparent window and a second position wherein the transparent window is unblocked so that the flexible container can be viewed prior to use.

16. The apparatus of claim 1, wherein: the roller has a rotational axis, and the relative movement between the roller and the container is a relative longitudinal movement in a longitudinal direction transverse to the rotational axis, and the container is longitudinally fixed relative to the housing during at least part of the relative longitudinal movement between the roller and the container.

17. The apparatus of claim 1, wherein: the roller includes two spaced co-axial roller portions; and the needle extends between the roller portions.

* * * * *